(12) United States Patent
Ramamurthy

(10) Patent No.: US 11,857,812 B2
(45) Date of Patent: Jan. 2, 2024

(54) ULTRASOUND GUIDED OPENING OF BLOOD-BRAIN BARRIER

(71) Applicant: Cordance Medical Inc., Mountain View, CA (US)

(72) Inventor: Bhaskar Ramamurthy, Mountain View, CA (US)

(73) Assignee: Cordance Medical Inc., Mountain View, CA (US)

(*) Notice: Subject to any disclaimer, the term of this patent is extended or adjusted under 35 U.S.C. 154(b) by 0 days.

(21) Appl. No.: 18/146,028

(22) Filed: Dec. 23, 2022

(65) Prior Publication Data

US 2023/0128189 A1 Apr. 27, 2023

Related U.S. Application Data

(63) Continuation of application No. 16/322,437, filed as application No. PCT/US2017/044763 on Jul. 31, 2017, now Pat. No. 11,534,630.

(Continued)

(51) Int. Cl.
*A61N 7/00* (2006.01)
*A61B 8/06* (2006.01)
(Continued)

(52) U.S. Cl.
CPC ............... *A61N 7/00* (2013.01); *A61B 8/06* (2013.01); *A61B 8/08* (2013.01); *A61B 8/0816* (2013.01);
(Continued)

(58) Field of Classification Search
CPC .... A61N 7/00; A61N 7/02; A61N 2007/0021; A61N 2007/0039; A61N 2007/0052;
(Continued)

(56) References Cited

U.S. PATENT DOCUMENTS 5,797,849 A 8/1998 Vesely et al.
6,334,846 B1 * 1/2002 Ishibashi .............. A61B 8/5223
600/412

(Continued)

FOREIGN PATENT DOCUMENTS

CN 101797424 A 8/2010
CN 101810913 A 8/2010
(Continued)

OTHER PUBLICATIONS

Chinese Office Action dated Mar. 29, 2022, for corresponding CN Patent Application No. 201780047574.6.
(Continued)

*Primary Examiner* — Baisakhi Roy
*Assistant Examiner* — Kaitlyn E Sebastian
(74) *Attorney, Agent, or Firm* — Dicke, Billig & Czaja, PLLC

(57) ABSTRACT

An ultrasound treatment system operable to deliver ultrasound energy to a patient's brain, the system comprises a treatment ultrasound transducer comprising a plurality of treatment elements, the treatment ultrasound transducer locatable to deliver ultrasound into the head of the patient. The system further comprises a data store, one or more position sensors configured to detect relative movement between the head of the patient and the treatment ultrasound transducer, and a data processor.

20 Claims, 20 Drawing Sheets

Related U.S. Application Data

(60) Provisional application No. 62/369,208, filed on Aug. 1, 2016.

(51) Int. Cl.

| | | |
|---|---|---|
| *A61B 8/14* | (2006.01) | |
| *A61B 8/00* | (2006.01) | |
| *A61B 8/08* | (2006.01) | |
| *A61N 7/02* | (2006.01) | |
| *A61B 9/00* | (2006.01) | |

(52) U.S. Cl.
CPC ............ *A61B 8/145* (2013.01); *A61B 8/4461* (2013.01); *A61B 8/466* (2013.01); *A61B 8/469* (2013.01); *A61B 8/481* (2013.01); *A61B 8/5207* (2013.01); *A61B 8/5261* (2013.01); *A61B 9/00* (2013.01); *A61N 7/02* (2013.01); *A61N 2007/0021* (2013.01); *A61N 2007/0039* (2013.01); *A61N 2007/0052* (2013.01); *A61N 2007/0073* (2013.01); *A61N 2007/0078* (2013.01); *A61N 2007/0095* (2013.01)

(58) Field of Classification Search
CPC .... A61N 2007/0073; A61N 2007/0078; A61N 2007/0095; A61B 8/06; A61B 8/08; A61B 8/0816; A61B 8/145; A61B 8/4461; A61B 8/466; A61B 8/469; A61B 8/481; A61B 8/5207; A61B 8/5261; A61B 9/00
See application file for complete search history.

(56) References Cited

U.S. PATENT DOCUMENTS

| | | | |
|---|---|---|---|
| 7,713,200 | B1 | 5/2010 | Sarvazyan et al. |
| 9,392,992 | B2 | 7/2016 | Hsu et al. |
| 2004/0122323 | A1 | 6/2004 | Vortman et al. |
| 2006/0058671 | A1 | 3/2006 | Vitek et al. |
| 2006/0222221 | A1 | 10/2006 | Sathyanarayana |
| 2006/0241438 | A1 | 10/2006 | Wu et al. |
| 2006/0241529 | A1 | 10/2006 | Hynynen et al. |
| 2007/0265560 | A1 | 11/2007 | Soltani et al. |
| 2008/0004528 | A1 | 1/2008 | Fitzsimons et al. |
| 2008/0183077 | A1 | 7/2008 | Moreau-Gobard et al. |
| 2009/0069678 | A1 | 3/2009 | Taniyama et al. |
| 2009/0143704 | A1* | 6/2009 | Bonneau ............... A61F 5/0111 600/595 |
| 2010/0016707 | A1 | 1/2010 | Amara et al. |
| 2010/0036245 | A1 | 2/2010 | Yu et al. |
| 2010/0143241 | A1 | 6/2010 | Johnson et al. |
| 2010/0228126 | A1 | 9/2010 | Emery et al. |
| 2010/0249668 | A1 | 9/2010 | Zhou et al. |
| 2012/0165670 | A1 | 6/2012 | Shi et al. |
| 2012/0327075 | A1 | 12/2012 | Zagorchev et al. |
| 2013/0225994 | A1* | 8/2013 | Hsu ..................... A61B 8/085 600/438 |
| 2014/0058292 | A1* | 2/2014 | Alford .................... A61N 7/00 601/2 |
| 2014/0107540 | A1 | 4/2014 | Murakami |
| 2014/0257100 | A1 | 9/2014 | Zheng et al. |
| 2015/0065871 | A1* | 3/2015 | Konofagou .............. A61N 7/02 600/431 |
| 2015/0080926 | A1 | 3/2015 | Emery |
| 2015/0306423 | A1 | 10/2015 | Bharat et al. |
| 2016/0078623 | A1 | 3/2016 | Forzoni et al. |
| 2016/0151618 | A1 | 6/2016 | Powers et al. |
| 2016/0213352 | A1 | 7/2016 | Toji |
| 2016/0317129 | A1 | 11/2016 | Seip et al. |
| 2017/0065835 | A1 | 3/2017 | Park |
| 2019/0021666 | A1 | 1/2019 | Hynynen |

FOREIGN PATENT DOCUMENTS

| | | |
|---|---|---|
| CN | 102341147 A | 2/2012 |
| CN | 103285531 A | 9/2013 |
| CN | 105435378 A | 3/2016 |
| EP | 2072013 A1 | 6/2009 |
| EP | 3285675 A1 | 2/2018 |
| JP | 2008284144 A | 11/2008 |
| WO | 2004066856 A1 | 8/2004 |
| WO | 2011079177 A1 | 6/2011 |
| WO | 2015092604 A1 | 6/2015 |
| WO | 2016170427 A1 | 10/2016 |

OTHER PUBLICATIONS

Chinese Office Action dated Aug. 16, 2022, for corresponding CN Patent Application No. 201780047574.6 (with partial English Translation).

Extended European Search Report dated Mar. 11, 2020, for corresponding EP Patent Application No. 17837489.8.

Japanese Office Action dated Aug. 3, 2021, for corresponding JP Patent Application No. 2019-506422. (with English translation) 8 pgs.

Hamzelou, "Blood bubbles promise new treatments for brain disease", New Scientist (Nov. 10, 2010), https://www.newscientist.com/article/mg20827864-500-blood-bubbles-promise-new-treatments-for-brain-disease.

Hamzelou, "Microbubbles open brain's barrier to make chemo more effective", New Scientist (Jun. 15, 2016), https://www.newscientist.com/article/2093829-microbubbles-open-brains-barrier-to-make-chemo-more-effective.

International Search Report and Written Opinion for corresponding PCT/US2017/044763 dated Oct. 12, 2017.

Nadrljanski (n.d.), "Ultrasound frequencies", Radiology Reference Article (Mar. 31, 2020), https://radiopaedia.org/articles/ultrasound-frequencies?lang=us.

Samuel, "Ultrasound used to target drug delivery in the brain", New Scientist (Dec. 5, 2001), https://www.newscientist.com/article/dn1644-ultrasound-used-to-target-drug-delivery-in-the-brain.

Thomson, "Human brain's ultimate barrier to open for first time", New Scientist (Jun. 18, 2014), https://www.newscientist.com/article/mg22229742-400-human-brains-ultimate-barrier-to-open-for-first-time.

Thomson, "Ultrasound prises open brain's protective barrier for first time", New Scientist (Nov. 10, 2015), https://www.newscientist.com/article/dn28474-ultrasound-prises-open-brains-protective-barrier-for-first-time.

Westphal, "Sound unlocks the brain", New Scientist (Jul. 31, 2002), https://www.eurekalert.org/pub_releases/2002-07/ns-sut073102.php.

* cited by examiner

ULTRASOUND GUIDED OPENING OF BLOOD-BRAIN BARRIER

CROSS-REFERENCE TO RELATED APPLICATION

This application is a Continuation of U.S. patent application Ser. No. 16/322,437, filed Jan. 31, 2019, which is the U.S. National Stage filing under 35 U.S.C. § 371 of PCT/US2017/044763, filed Jul. 31, 2017, each of which claims benefit to U.S. Provisional Application No. 62/369,208, filed Aug. 1, 2016, and which are each incorporated herein by reference in their entireties.

BACKGROUND

Drugs are an important treatment modality for a range of diseases affecting the brain including brain cancers. Treatment of diseases of the brain is challenging in part due to the structure of the blood-brain barrier. The blood-brain barrier separates circulating blood from other brain tissue, and has a highly selective permeability. This barrier prevents about 98% of small molecules and nearly 100% of large molecules from entering the brain from the bloodstream. This makes it difficult to transport drugs to various tissues of the brain, e.g. to tumor sites.

The blood-brain barrier can be caused to open in certain regions by delivering ultrasonic energy to those regions, thereby increasing the possibility for a wider range of molecules of different sizes to pass from the bloodstream into tissues of the brain. This technique may be applied to allow drugs to be delivered to the brain. In the current state-of-the-art techniques to deliver drugs to the brain, magnetic resonance imaging (MRI) may be utilized in combination with ultrasound based delivery mechanisms. In these techniques, MRI is used to inform the ultrasound based mechanism where within the brain to focus ultrasonic energy.

In these techniques, MRI scans are typically obtained at two different stages. The first stage, called the "pre-operation" or "pre-op" stage, is before the "operation" or "treatment" (the time period where the drug is actively delivered to the patient). The second stage, called "intra-operation" or "intra-op", is during the operation. These techniques typically require the concurrent operation of MRI scanners to identify target regions for treatment within a patient's head and ultrasound transducer(s) to deliver energy to effect the opening of the blood-brain barrier.

FIG. 1 shows schematically a prior art example drug delivery system 100. Ultrasound system 105 is coupled to ultrasound transducer 110, which is located adjacent to patient P's head. Ultrasound transducer 110 may be situated so that it can be operated to transmit ultrasonic energy to selected area(s) in patient P's brain. Ultrasound transducer 110 may comprise one or more ultrasonic elements that are operable to deliver ultrasonic energy to a target region. MRI system 120 may include MRI scanner 125 which is operable to provide images of patient P's head during treatment. Patient P's head is typically placed within bore 135 of MRI scanner 125 during scanning. MRI images may be used to control the operation of ultrasound system 105 to insonate the target region. Drugs 130 delivered intravenously to patient P may then enter tissues in the targeted area of patient P's brain.

Reliance on MRI during the delivery of ultrasound reduces the broad applicability of this technique. MRI scanning typically involves inserting the patient's body part of interest (here the head) into bore 135 of MRI scanner 125. This often involves inserting the patient deep in the bore so that the head is at the center of the MRI scanner. The tight confines of the bore inhibit the treating physician's freedom in manipulating various apparatus during treatment, such as ultrasound transducer 110.

Further, the above configuration may present significant challenges for the patient. As an example, some patients may experience extreme discomfort if they are claustrophobic and are forced to be within the bore of the MRI system during treatment. Additionally, it is very expensive to acquire and operate an MRI scanner. These high costs limit access to MRI scanners.

There remains a need for practical and effective methods, systems and apparatus that can be applied to facilitate the delivery of molecules across selected portions of the blood-brain barrier.

SUMMARY

This invention has a number of aspects that may be applied together, individually and in any sub-combination. These include, without limitation:
 Apparatus and methods for selectively opening the blood-brain barrier in a patient;
 Apparatus and methods for delivering drugs to the brain of a patient;
 Apparatus and methods for registering ultrasound images with pre-operation images;
 Apparatus and methods for identifying areas of treatment in a patient;
 Apparatus and methods for delivering ultrasound energy to a patient; and
 Controllers for apparatus and methods for delivering drugs to the brain of a patient.

Some aspects of the invention provide systems to deliver ultrasound to one or more regions of the brain.

An example aspect of the invention provides a system operable to deliver ultrasound energy to a patient's brain. The ultrasound energy may facilitate opening of the blood brain barrier. Delivery of the ultrasound energy may be coordinated with delivery of a drug which may enter the patient's brain upon opening of the blood brain barrier, thereby facilitating treatment. The system comprises: an imaging ultrasound transducer; a treatment ultrasound transducer; an ultrasound machine connected to operate the imaging ultrasound transducer to generate one or more ultrasound images; and a data processor. the data processor is configured to: process one of the ultrasound images with a corresponding previously obtained image to register the previously-obtained image to the ultrasound image to yield a transformation relating coordinates in a frame of reference of the previously obtained image to coordinates in a frame of reference of the ultrasound image; using the transformation, determine coordinates of at least one target region in the frame of reference of the ultrasound image; and based on the coordinates of the at least one target region, determine a target location for the treatment ultrasound transducer to deliver ultrasound energy to the at least one target region. The system may include a data store in which the previously obtained image may be provided.

The treatment transducer optionally comprises one or more transducer elements that are connected to transmit ultrasound signals and are not connected to a receiving circuit. In some embodiments the treatment transducer has a frequency of operation lower than a frequency of operation of the imaging transducer.

The system may comprise a robotic manipulator connected to selectively position one or both of the imaging transducer and the treatment transducer. In such embodiments the imaging ultrasound transducer may be carried by the robotic manipulator and the data processor may be configured to control the robotic manipulator to position the imaging ultrasound transducer at an imaging location to generate the one or more images. The imaging location may correspond to a low attenuation acoustic window in the skull of the patient. In such embodiments the treatment ultrasound transducer may be carried by the robotic manipulator and the data processor may be configured to control the robotic manipulator to position the treatment ultrasound transducer at a target location. The target location may be determined in a frame of reference of the robotic manipulator using the transformation.

In some embodiments the processor is configured to process the previously obtained image to determine a tangent plane to a patient's skull at the target location and to operate the robotic manipulator to orient the treatment transducer perpendicular to the tangent plane.

In some embodiments the system comprises a sensor outputting one or more of: position and orientation; the sensor attached to one or more of: the imaging transducer and the treatment transducer; and the data processor is configured to process an output signal from the position sensor to determine when the treatment transducer is at the target location.

Various forms for the imaging and treatment transducers are possible. In some embodiments the system comprises a support shaped to define a cavity dimensioned to receive a patient's head and a plurality of transducer elements are distributed over the support. In such embodiments the imaging ultrasound transducer may comprise a first subset of the transducer elements and the treatment ultrasound transducer may comprise a second subset of the transducer elements. The treatment ultrasound transducer optionally comprises a plurality of subsets of the transducer elements each of the plurality of subsets being configured to deliver ultrasound energy to the same target region. The imaging ultrasound transducer optionally comprises a plurality of subsets of the transducer elements. The data processor may be configured to select the second subset of the transducer elements from the transducer elements based on the target location. The data processor may be configured to determine a number of the transducer elements to include in the second subset of the transducer elements based at least in part on a distance between the target region and the target location.

The support optionally comprises one or more mechanical sub-structures, each mechanical sub-structure carrying one or more of the transducer elements. Actuators may be coupled to adjust a position and/or orientation of the sub-structure. The system may be configured to control the actuators to place the transducer elements in desired positions and orientations, for example to bring the transducer elements into contact with a patient's head and/or to orient the transducer elements perpendicular to a tangent plane to the patient's head. The data processor may be configured to process the previously obtained image to determine a tangent plane to a patient's skull at the target location and to operate the one or more actuators orient the substructure such that the transducer elements carried by the sub-structure are oriented perpendicular to the tangent plane.

In some embodiments the data processor is configured to calculate an estimated attenuation of ultrasound travelling between the target location and the target region and to determine at least one of: a number of the transducer elements to include in the second subset of the transducer elements and a power level for driving the transducer elements in the second subset of transducer elements based at least in part on the estimated attenuation.

In some embodiments the system comprises plural (e.g. two or three or more) treatment transducers and the system is configured to deliver ultrasound to the target region by the plural treatment transducers in succession. This can reduce the buildup of standing waves. In some embodiments each of the plural treatment transducers comprises plural transducer elements distributed over an area. The areas of two or more of the plural treatment transducers may optionally overlap. In some embodiments the system is configured to substantially continuously insonate a target region for a treatment period comprising plural sub periods by operating different sets of one or more of the plural treatment transducers in different ones of the sub periods. Each of the treatment transducers may be controlled to focus ultrasound energy on the target region. Ultrasound energy may be focused on a target region through the use of beam steering, acoustic lenses and/or other techniques for concentrating ultrasound as known in the art.

In some embodiments the system comprises a drug delivery system and the data processor is configured to trigger operation of the drug delivery system. For example, the data processor may be configured to trigger operation of the treatment ultrasound transducer a predetermined time after triggering operation of the drug delivery system and/or upon detecting that a drug has been carried in the bloodstream to the target region (e.g. by detecting acoustic signatures of microbubbles associated with the drug originating from the target region—the treatment ultrasound transducer may emit first ultrasound signals which generate the acoustic signatures upon interaction with the microbubbles until the microbubbles are detected and then be switched to delivering ultrasound energy to facilitate treatment).

A source of one or more of first and second microbubbles may be connected to the drug delivery system. The first microbubbles may be configured to amplify signals reflected back to the imaging transducer. The second microbubbles may be configured to vibrate or break when receiving ultrasound energy from the treatment transducer. The second microbubbles may contain one or more drugs.

The data store may store predetermined treatment ultrasound parameters for a plurality of drugs. Different ultrasound parameters may be stored for different drugs or different drug delivery modalities (e.g. with or without microbubbles, different types of microbubbles). In some embodiments the ultrasound system comprises a reader operative to read drug-identification information identifying one of the plurality of drugs from a machine-readable tag and the data processor is configured to use the drug-identification information to retrieve predetermined treatment ultrasound parameters corresponding to the one of the plurality of drugs corresponding to the drug-identification information. The reader may comprise, for example a bar code reader, a QR code reader, or a RFID, reader.

Some embodiments comprise an electromagnetic (EM) tracking system operative to track a position of one or both of the imaging transducer and the treatment transducer. For example, the EM tracking system may comprise an EM transmitter and an EM sensor attached to one or more of: the imaging transducer and the treatment transducer.

In some embodiments the data processor is configured to obtain the transformation by: processing the previously obtained image to obtain reconstructed images along one or more planes and identifying a common structure in the reconstructed images and the ultrasound image; determining a correlation value between each of the reconstructed images and the ultrasound image, selecting one of the one reconstructed images having the greatest correlation value above a threshold, and assigning the common structure in the selected reconstructed image coordinates of the common structure in the ultrasound image in a frame of reference of the ultrasound image. The data processor may be configured to find the correlation value by performing one or more of: changing a scale factor, changing an orientation angle and rotating by an angle on one or more of the reconstructed images.

Another example aspect of the invention provides a method for configuring an ultrasound machine. The method comprises: obtaining an ultrasound image that includes one or more structures in a patient's head using an imaging ultrasound transducer and, by a data processor: registering a previously-obtained image of the patient's head to the ultrasound image to yield a transformation relating coordinates in a frame of reference of the previously obtained image to coordinates in a frame of reference of the ultrasound image, wherein the previously-obtained image includes the one or more structures; using the transformation determining coordinates of at least one target region in the frame of reference of the ultrasound image; and based on the coordinates of the at least one target region determining a location for at least one ultrasound treatment transducer to deliver ultrasound energy to the at least one target region. The one or more structures may comprise, for example, one or more of: circle of Willis, ventricles, corpus callosum, dental implants, surgical screws, and orthopaedic hardware.

In some embodiments obtaining the transformation comprises: processing the previously obtained image to obtain reconstructed images along one or more planes and identifying a common structure in the reconstructed images and the ultrasound image; determining a correlation value between each of the reconstructed images and the ultrasound image, selecting one of the one reconstructed images having the greatest correlation value above a threshold, and assigning the common structure in the selected reconstructed image coordinates of the common structure in the ultrasound image in a frame of reference of the ultrasound image.

The previously obtained image may, for example, comprise a magnetic resonance image (MRI) or a computed tomography (CT) image. The method may receive user input specifying the location of the target region relative to the previously obtained image. Some embodiments involve operating a robotic manipulator to place the ultrasound imaging transducer or the ultrasound treatment transducer at the determined location. Other embodiments involve manual placement of the ultrasound imaging transducer or the ultrasound treatment transducer at the determined location by a human operator.

In some embodiments the method comprise configuring a plurality of transducer elements in the vicinity of the determined location to be operated as the treatment transducer.

The imaging transducer may be located adjacent to a low attenuation acoustic window in a patient's skull. The low attenuation acoustic window may, for example, comprise the temple, back of the head or behind an eye of the patient.

Some embodiments comprise commanding a drug delivery system to deliver to the patient microbubbles configured to vibrate or break when receiving ultrasound energy from the treatment transducer.

Another example aspect of the invention provides an ultrasound transducer assembly comprising: one or more first transducer elements; one or more second transducer elements; one or more electronic channels operable to drive the first and second transducer elements to emit ultrasound, each of the electronic channels coupled to drive one or more of the first and second transducer elements; the first transducer elements each coupled to a receive circuit and the second transducer elements not connected to receive circuits. The ultrasound transducer assembly optionally comprises a support carrying the first and second transducer elements and formed to provide a cavity dimensioned to receive the patient's head. The transducer elements may be uniformly distributed on the support.

Another example aspect provides a controller for a drug delivery system. The controller comprises a data processor configured to: register a previously-obtained image of a patient's head to an ultrasound image that includes one or more structures in the patient's head to yield a transformation relating coordinates in a frame of reference of the previously obtained image to coordinates in a frame of reference of the ultrasound image, wherein the previously-obtained image includes the one or more structures; using the transformation determining coordinates of at least one target region in the frame of reference of the ultrasound image; and based on the coordinates of the at least one target region determining a location for at least one ultrasound treatment transducer to deliver ultrasound energy to the at least one target region. It is not necessary for the ultrasound image to include the target region. The ultrasound image may have a much smaller field of view than the previously obtained image. The controller may optionally be configured to control a drug delivery system and/or a robotic manipulator for positioning one or more ultrasound transducers or transducer elements.

Another example aspect provides a method for delivering a drug to a target region within a person's brain, the method comprises: obtaining an ultrasound image of one or more structures within the person's head using one or more imaging ultrasound transducers; registering the ultrasound image to a previously acquired image of the person's head; based on the registering determining a location of the target region relative to the one or more imaging ultrasound transducers; administering the drug into the patient's bloodstream and controlling one or more treatment ultrasound transducers to deliver ultrasound energy to the target region using known positions of the treatment ultrasound transducers relative to the imaging ultrasound transducers and the location of the target region relative to the one or more imaging ultrasound transducers.

Further aspects of the invention and features of example embodiments of the invention are described below and/or illustrated in the accompanying drawings.

BRIEF DESCRIPTION OF THE DRAWINGS

Non-limiting example embodiments are illustrated in the appended drawings.

DETAILED DESCRIPTION

Figure 1:
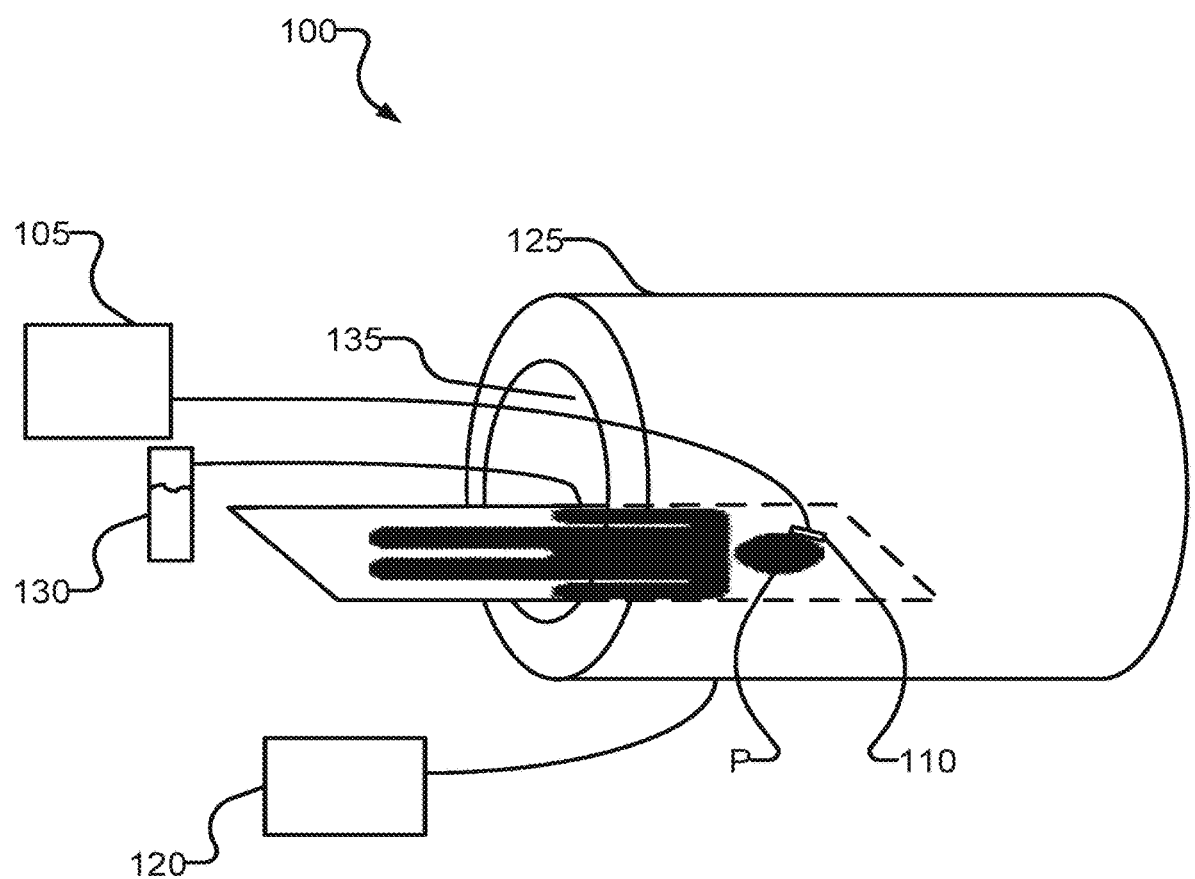
FIG. 1 is a schematic illustration showing an example prior art drug delivery system that uses MRI scanning during treatment to guide the placement of ultrasound transducers.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Some aspects of this invention provide systems and methods which use ultrasound to produce one or more ultrasound images of a part of a patient's head. These one or more images may be registered with previously acquired images by identifying one or more structures that are present in both the ultrasound images and the previously acquired images ("common structures"). The registered images may then be used locate one or more target regions relative to transducers used to acquire the ultrasound image(s). The target regions may have known locations relative to the common structures. Ultrasound may then be delivered to the target region(s) to open the blood-brain barrier to allow drugs to enter brain tissue. Delivery of the ultrasound to the target region(s) may be coordinated with injection of one or more drugs into the patient's circulatory system. The ultrasound energy may be focused onto the target regions such that the blood brain barrier is opened selectively in the target regions.

Methods and apparatus as described herein may optionally and beneficially apply two or more ultrasound transducers. One or more of the transducers is operable for acquiring images of structures in the patient's head including parts of the brain ("imaging transducers"). One or more of the transducers is operable to deliver ultrasonic energy to promote the selective opening of the blood-brain barrier in target regions ("treatment transducers").

Imaging the brain with ultrasound or transmitting ultrasonic energy into the brain is a challenge because the skull attenuates ultrasound energy. Certain embodiments of the present invention exploit the fact that the skull has some areas where the attenuation of ultrasound is lower than in other areas of the skull. These areas include, but are not limited to, the temples of the head near the ears and behind the eyes and in the back of the head. The skull in these areas tends to be thinner compared to the rest of the skull. Thus, ultrasonic energy can pass more easily through these areas compared to other areas of the skull. The areas where the attenuation of ultrasound is lower compared to the rest of the skull are referred to herein as "low attenuation acoustic windows". Ultrasound energy may be transmitted into the brain via low attenuation acoustic windows and/or echo signals may be received from structures within the brain via low attenuation acoustic windows more easily than via other areas of the skull.

Ultrasound imaging relies on the transmission of ultrasound energy into the patient's body, and subsequently, detecting the energy that is reflected by internal tissue. Regions in the head that can be imaged by ultrasound are limited, as there are few low attenuation acoustic windows in the skull. Even through these low attenuation acoustic windows, the structures that can be effectively imaged are limited.

Diagnostic imaging is often conducted when diagnosing a patient for brain tumors. As such, brain images acquired using other modalities, such as MRI or computed tomography (CT), are available for many patients. MRI and CT do not suffer from the same penetration issues through the skull as ultrasound imaging. MRI scans of the brain are therefore able to image the entire brain, including the same structure (s) that may be imaged with an ultrasound transducer through a low attenuation acoustic window. Various implementations of the present invention apply the realization that the same structure(s) may be imaged with two different imaging modalities.

Certain structures may be imaged by ultrasound imaging performed through a low attenuation acoustic window such as one or both temples. These structures may include, for example, structures of the brain such as the circle of Willis, ventricles, and the corpus callosum and/or other structures in known positions relative to the patient's brain (e.g. dental implants, surgical screws, orthopaedic hardware affixed to the patient's skull or the like). All or parts of these same structures may be visible in a pre-operation MRI or CT scan. In some embodiments of the invention, ultrasound images obtained by one or more imaging ultrasound transducers via low attenuation acoustic windows are "registered" to MRI or CT images obtained of the same patient. Registration may be performed by processing the images of common structure(s) imaged in both imaging modalities.

Regions where ultrasound energy is to be delivered to facilitate treatment ("target regions") generally have known locations in pre-op images (e.g. MRI and/or CT scans). The location of a target region may be found in a coordinate system of the presently obtained ultrasound image through the process of registration. It is not necessary for the target region(s) to be in the field of view of the ultrasound image. Ultrasound energy may then be delivered to the target region(s) using one or more treatment ultrasound transducers or transducer elements that have known position(s) and orientation(s) relative to the ultrasound image.

The known position(s) and orientation(s) of the treatment transducer(s) and the imaging transducer(s) may be maintained by any one or more of: mounting the treatment transducers and imaging transducers used to obtain the ultrasound image to a common fixed support structure; mounting the treatment transducers and the imaging transducers to a support structure (e.g. an articulated arm or other manipulator) having one or more joints that are movable and tracking positions of the joint(s); manually positioning the treatment transducers and imaging transducers by an operator; and using a position tracking system (e.g. an electromagnetic position tracker) to monitor relative positions and orientations of the treatment transducer(s) and the imaging transducer(s). Example implementations which exploit these approaches are described herein.

Figure 2:
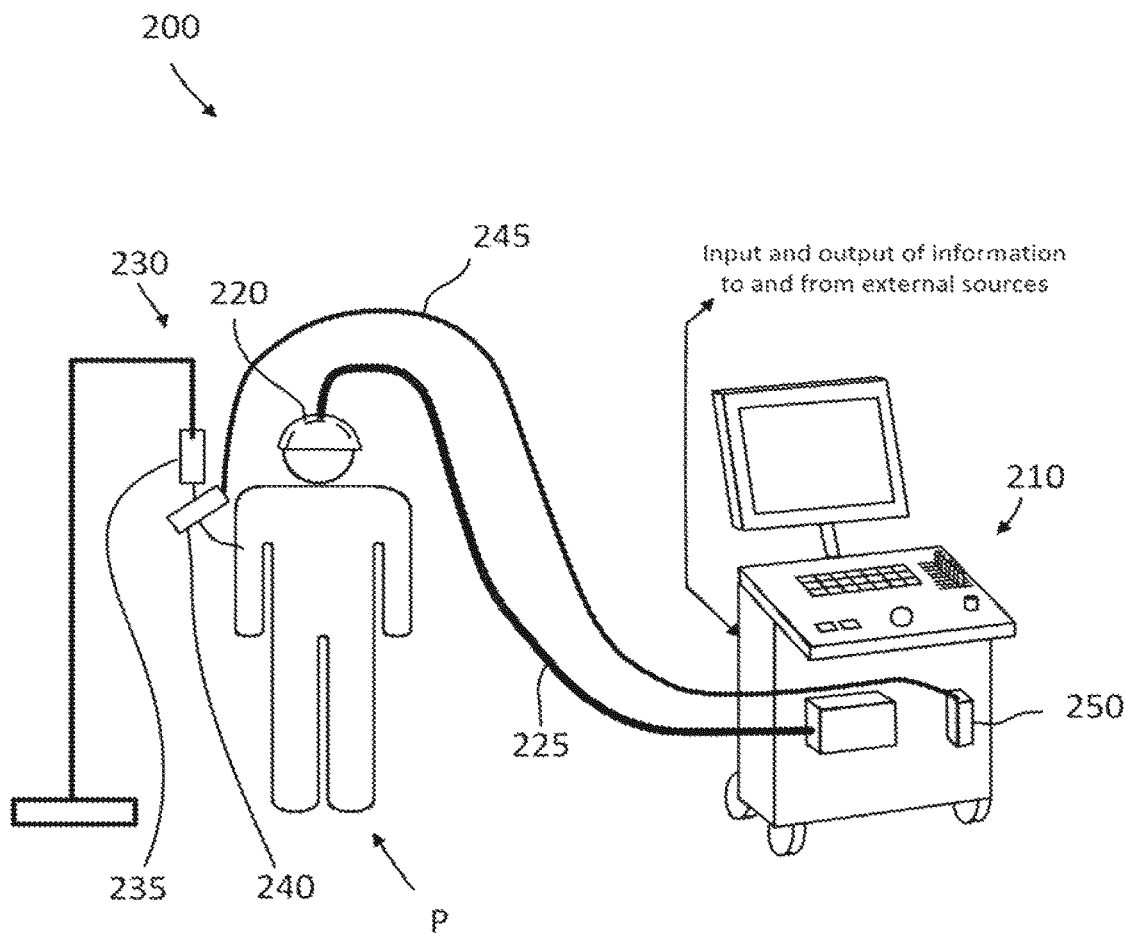
FIG. 2 is a schematic illustration showing an ultrasound system according to an example embodiment that is operable to deliver a drug to a patient.

FIG. 2 shows an example system 200 that may be used for imaging at least a portion of a patient P's brain and subsequently delivering ultrasound to selectively open patient P's blood-brain barrier. System 200 does not require use of an MRI scanner during treatment (the "intra-op period"). System 200 includes an ultrasound system 210. Ultrasound system 210 is coupled to ultrasound transducer assembly 220 via transducer cable 225. Ultrasound transducer assembly 220 is shown to be in the shape of a helmet having a concave opening dimensioned to receive at least the top part of a patient's head. Other configurations are not excluded. Ultrasound transducer assembly 220 may comprise one or more imaging transducers and/or treatment transducer elements.

The illustrated system 200 includes an electronically controlled intravenous (IV) drug delivery system 230. In this non-limiting example, IV system 230 is shown to include one IV bag 235 and an electronic valve or valve system 240. In other embodiments, IV system 230 may comprise multiple bags 235. Electronic valve 240 may be used to control the rate of flow of the contents of the one or more bags in IV system 230. Electronic valve 240 may be controlled by ultrasound system 210 which may send control signals via control line 245. Signal interconnect module 250 may send and receive signals from external and peripheral devices, such as electronic valve 240, and communicate with a peripherals and I/O module within ultrasound system 210 as will be discussed later. Signal interconnect module 250 may also include the ability to connect and disconnect cables that connect to external devices and peripherals.

Overview

Figure 3:
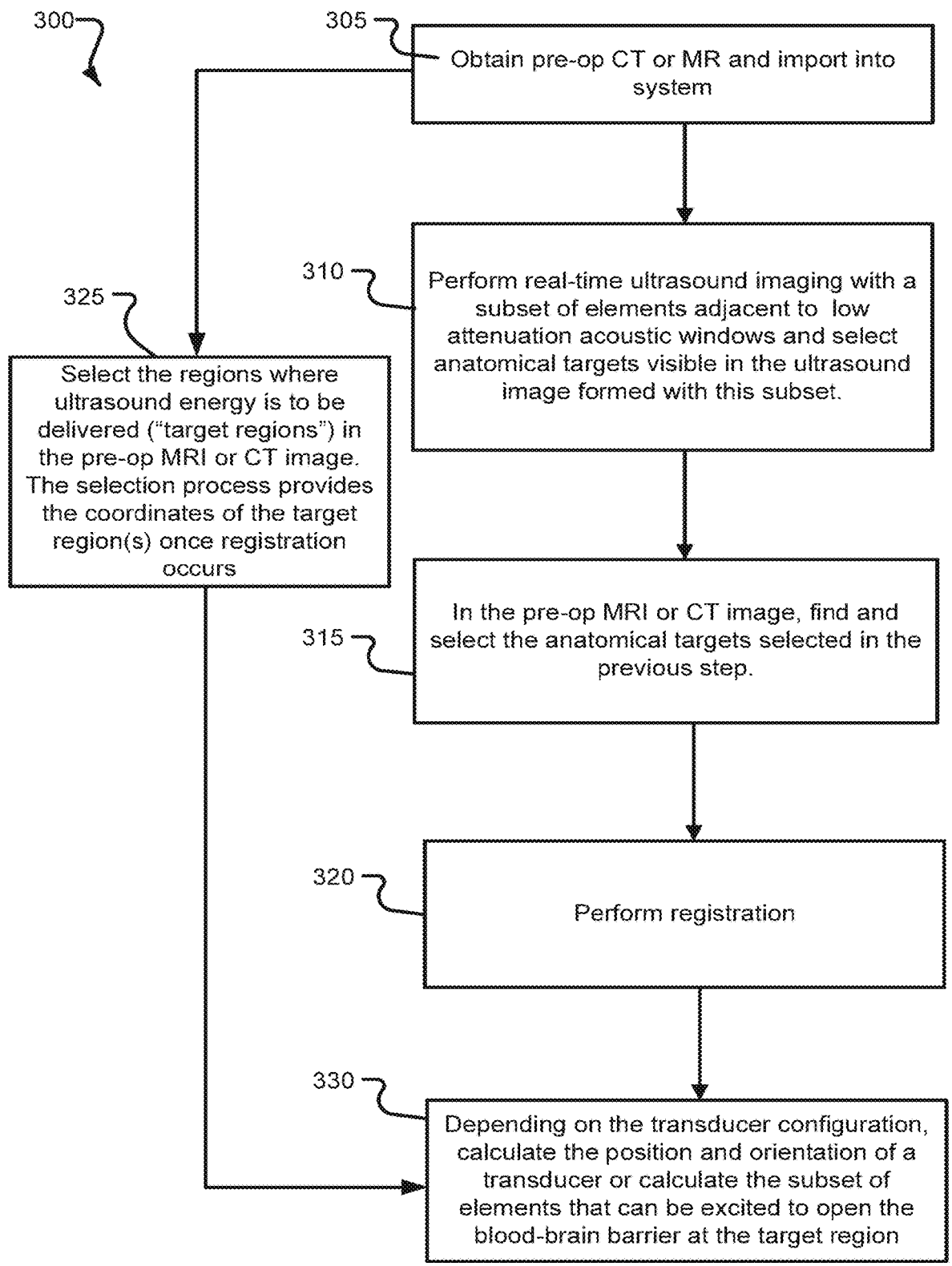
FIG. 3 is a flow chart for an example method that exploits low attenuation acoustic windows to guide ultrasound to target regions.

FIG. 3 is a flowchart showing a non-limiting example method 300 that may be performed to determine the position(s) and orientation(s) for one or more treatment transducers that may be configured to deliver ultrasound in conjunction with treating a patient. At step 305, pre-op CT or MRI images are imported into a system 200. System 200 may be applied for imaging at least a portion of a patient brain and subsequently delivering ultrasound to selectively open the patient's blood-brain barrier. In the illustrated embodiment ultrasound system 210 includes a controller that provides overall control over system 200 and the pre-op images are provided in or imported into a data store accessible by ultrasound system 210.

Step 310 performs ultrasound imaging to obtain images of certain target structures (e.g. circle of Willis). The imaging may be performed in real-time and monitored by a human operator. This may beneficially be done by placing imaging transducer(s) to obtain the ultrasound images through low attenuation acoustic windows in the patient's skull.

Step 310 also identifies common structures that may be used for registration. Step 320 registers the ultrasound image and the pre-op image by comparing the position and orientation of the common structure(s) in the ultrasound image to the position and orientation of the same common structure visible in the pre-op images. The registration yields a transformation by which coordinates of points in the pre-op images may be transformed to yield coordinates of the same points in a frame of reference of the ultrasound image or vice versa.

At step 325, target regions where ultrasound is to be delivered are identified. Target regions may be selected in the pre-op image. Step 325 may comprise, for example, identifying a tumor or other diseased area requiring treatment, or an area of the blood-brain barrier to be opened. This selection may occur at any time after the pre-op image(s) are obtained. In some cases one or more target regions are identified outside of system 200, for example using treatment planning software. In such cases data identifying the target region(s) may be imported into system 200 in step 305.

The current desired coordinates to which ultrasound energy should be delivered by one or more treatment transducers will be known once registration has occurred and the target region is selected. The position(s) and orientation(s) of the one or more treatment transducers may then be calculated at step 330. Step 330 may comprise, for example, determining desired coordinates at which one or more treatment transducers should be placed and/or selection from among a plurality of transducers or transducer elements of transducers and/or transducer elements to be used to deliver ultrasound energy to a specific target region. Method 300 may be performed, for example, with any of the ultrasound system configurations discussed below.

Ultrasound System Apparatus

Figure 4:
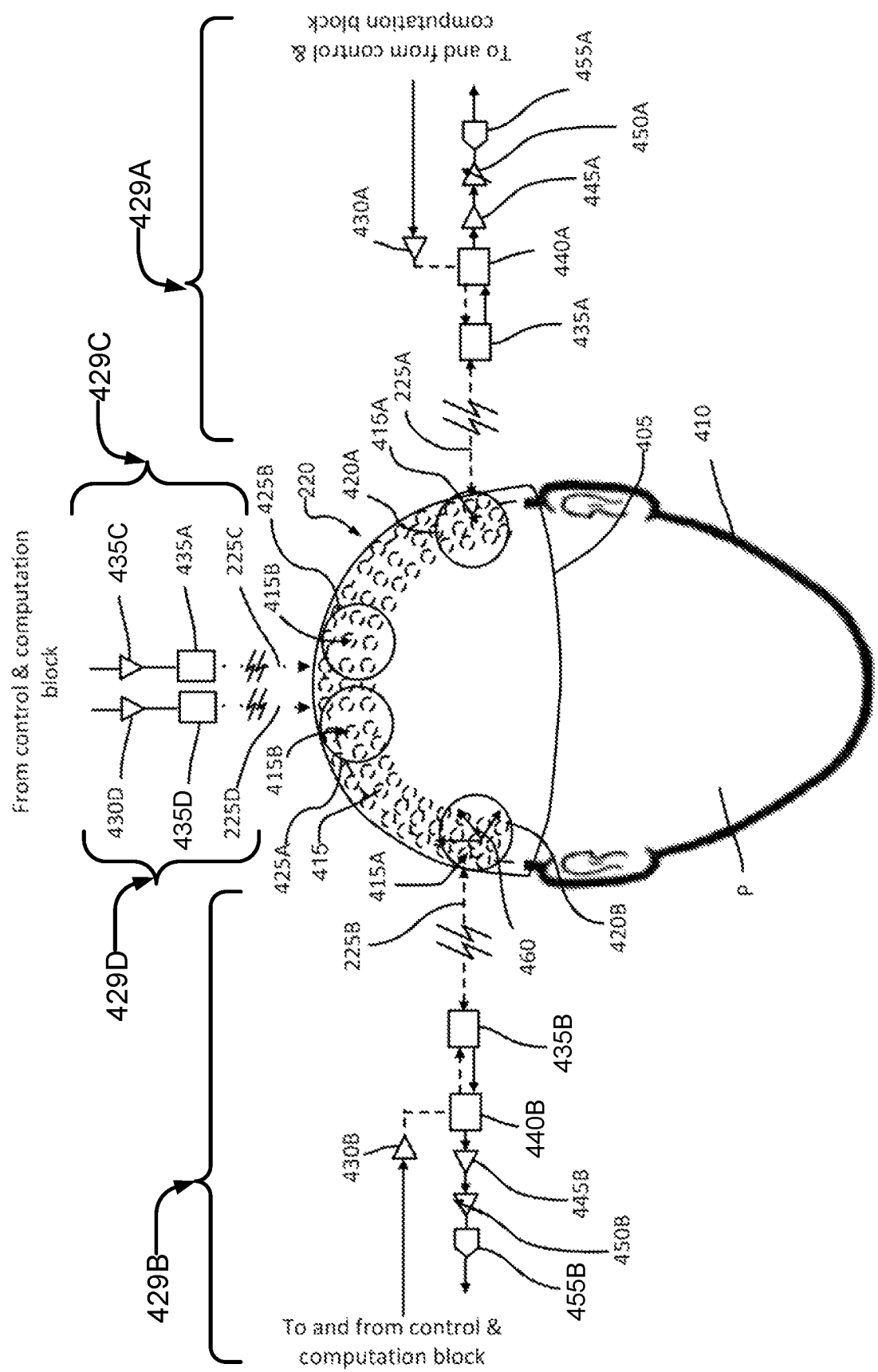
FIG. 4 is a schematic illustration of apparatus according to an example embodiment that includes showing multiple ultrasound transducers that are configured to either only transmit, or to transmit and receive ultrasound energy.

FIG. 4 shows an example ultrasound transducer assembly 220 which may be placed over patient P's head. Ultrasound transducer assembly 220 includes a support structure 405 that holds and positions plural transducer elements in desired locations on the patient's head. The portion of patient P's head 410 that is behind ultrasound transducer assembly 220 is shown in bold dashed lines.

Ultrasound transducer assembly 220 comprises transducer elements 415. Optionally, elements 415 include imaging elements 415A that are adapted for imaging, and treatment elements 415B that are adapted for delivering ultrasound to facilitate treatment.

Groups of elements 415, or subsets, may be configured to perform a common function such as imaging the brain or delivering ultrasound to facilitate treatment (e.g. by opening the blood-brain barrier). In FIG. 4, some imaging elements 415A are included in each of subsets 420A and 420B. Some treatment elements 415B are included in each of subsets 425A and 425B.

Elements 415A and 415B may differ from one another in various ways including one or more of:
location (e.g. imaging elements 415A may be clustered or concentrated near one or more low attenuation acoustic windows while elements 4156 may be more widely distributed—in cases where the approximate location of one or more target regions is known in advance transducer assembly 220 may optionally be customized by concentrating elements 415B in areas suitable for delivering ultrasound energy to the target region(s));

connection to receiving circuits (e.g. imaging elements 415A are connected to receiving circuits which may detect ultrasound echoes while treatment elements 415B are optionally not connected to receive circuits);

connection to different transmitting circuits (e.g. treatment elements and imaging elements may be driven by differently designed driving circuits. The treatment elements may, for example, be driven by higher-power driving circuits optimized to operate at lower frequencies than the imaging elements);

power (e.g. treatment elements 415B may be constructed to generate higher power ultrasound than imaging elements 415A);

optimum operating frequency (e.g. treatment elements 415B may operate most efficiently at lower frequencies than imaging elements 415A);

size (e.g. treatment elements 415B may be larger and/or more widely spaced apart than imaging elements 415A);

configuration (e.g. treatment elements 415B may include acoustic lenses that focus at different depth(s) than imaging elements 415A).

Imaging elements 415A may be located at positions in transducer assembly 220 that are adjacent to low attenuation acoustic windows when ultrasound transducer assembly 220 is worn by patient P. This is illustrated by subsets 420A and 420B in FIG. 4 being located at the temples. Subsets of transducer elements that are configured to produce images may generally be referred to as "imaging subsets".

Subsets of transducer elements that are used to deliver ultrasound energy to facilitate treatment do not have to be situated near a low attenuation acoustic window. As such, "treatment subsets" may be selected to include those treatment elements at locations from which it is optimal to deliver ultrasound to a target region. Treatment subsets will often be at different locations from imaging subsets. This is illustrated by subsets 425A and 425B. In some embodiments transducer 220 includes a large number of treatment elements located at a wide range of positions from which ultrasound energy may be delivered to a wide range of target regions. From this large number of treatment elements a subset may be chosen to deliver ultrasound energy to specific target region(s).

Subsets of transducer elements include enough elements to accomplish their task, be it imaging or delivering ultrasound energy that facilitates treatment. The organization of the elements within a subset may also be a factor for effective operation. In FIG. 4, subsets 420A, 420B, 425A, and 425B are pictured to be circular, with the individual elements organized in a 2D array. However, element groupings within a subset need not be circular in nature. They may be of any appropriate shape such as a curved-linear format. In an example embodiment, the preferred size of a subset is in the range of 2 to 3 cm in diameter. Individual transducer elements 415 may have a range of shapes. Each element may have a circular cross section, although other shapes such as rectangular shapes are not excluded.

Different subsets may differ from one another in various ways including, the number of transducer elements included in the subset, the shape and size of the area over which the included transducer elements are distributed and the way in which the transducer elements are operated to perform a desired function (e.g. imaging or delivering ultrasound to facilitate treatment).

Ultrasound Control Subsystems

Figure 5:
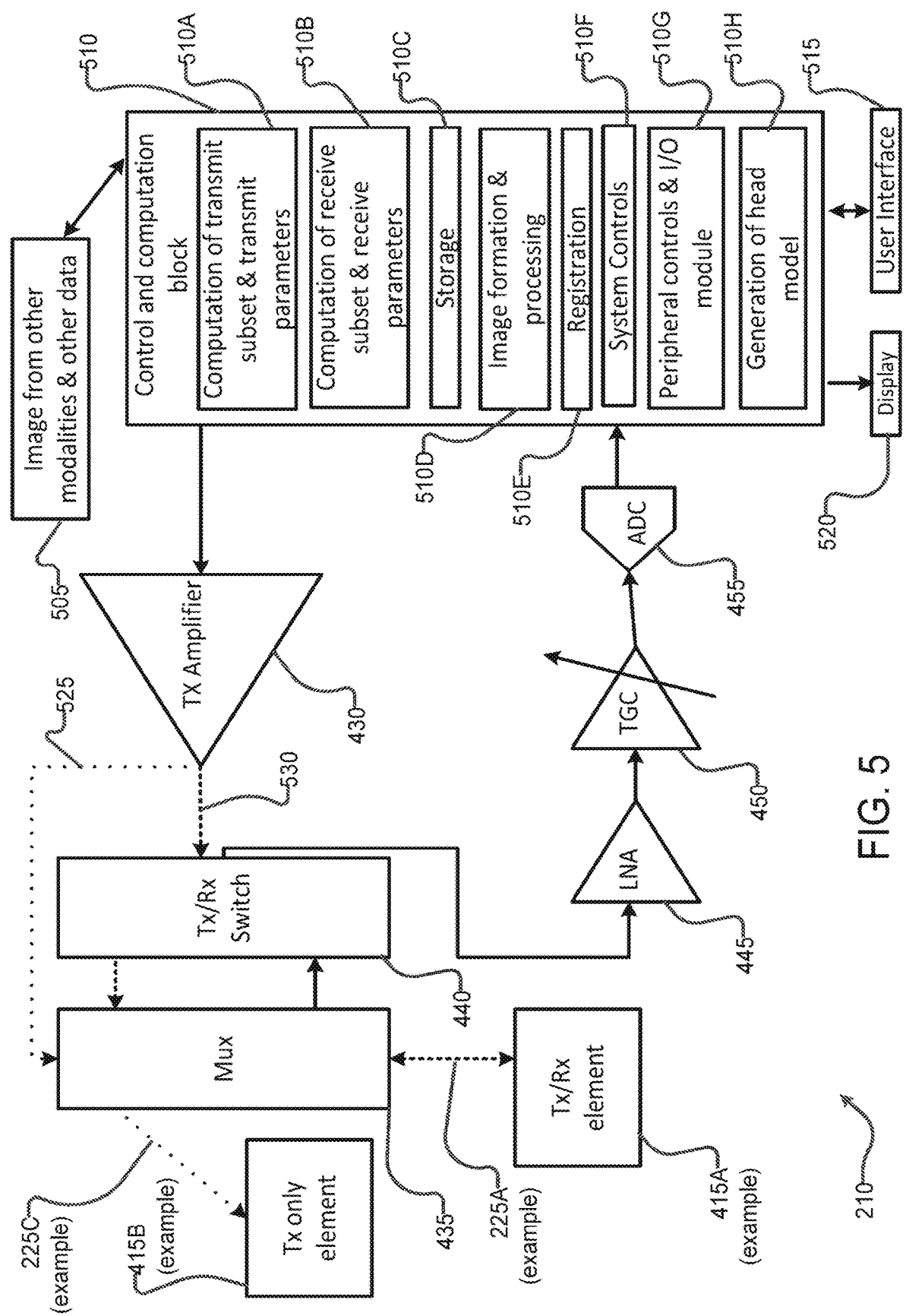
FIG. 5 is a block diagram of apparatus according to another example embodiment.

FIG. 5 illustrates the operation of a control subsystem of an ultrasound system 210 operable to image and deliver treatment to a patient's brain. Control subsystems as described herein may be applied to ultrasound systems having other configurations and/or supplied as stand-alone components. Block 505 comprises a data store that may contain images from other modalities (e.g. MRI or CT scans), as well as other data. Block 505 is in communication with control and computation block 510, which may include one or more modules. The modules within control and computation block 510 may be employed either individually, or in any combination or sub-combination with each other.

Module 510A generates control signals that affect operation of transducer elements that will be used for a transmit operation (i.e. where an element sends ultrasonic energy into the brain).

For example, block 510A may generate control signals that determine one or more of:
what transducer elements 415 or subset comprising transducer elements 415 will be used for a transmit operation;
what waveform(s) will be transmitted by transducer elements 415;
what transmit delays will be applied to individual transducer elements 415;
at what amplitude(s) will individual transducer elements 415 be driven;
what transmit apodization function will be applied to transducer elements 415;
at what time(s) will transducer elements 415 be operated to transmit ultrasound;
at what frequency(ies) will transducer elements 415 be driven;
etc.

Module 510A may include or have access to a data structure that indicates the locations of transducer elements 415. This data structure may be used in determination of what transducer elements 415 use for a particular transmit operation and/or to calculate transmit delays, for example.

Module 5106 generates control signals that affect operation of transducer elements that will be used for a receive operation (i.e. where an element receives echo signals from structures within the brain). Control signals from module 5106 may determine, for example, one or more of:
what transducer elements 415 are used to receive;
beamforming parameters;
receive apodization function;
receive gain;
receive depth;
image processing to be applied;
etc.

Storage module 510C includes a data store that may be used to store various information including, but not limited to, digitized radio-frequency (RF) data received at the elements that are configured to receive, images acquired from other modalities and transferred to ultrasound system 210, and intermediate or final results of computations performed within control and computation block 510.

Module 510D may perform computations related to image formation and image processing. Module 510D may apply any suitable technology for ultrasound image formation. In a non-limiting example of a computation related to image formation, RF data received from some or all imaging elements 415A may be summed in module 510D based on receive delays computed by module 510B. Images of the anatomy may be formed based on these sums. In a non-limiting example of a computation related to image processing, after the images are formed, they may be processed in various ways including, but not limited to, filtering, log compression, mapping to post-processing maps, etc.

Module 510E may perform various computations such as, but not limited to, computations with respect to registration of intra-op ultrasound images to images from other imaging modalities. The results of these computations may be applied to select and/or position transducers operable to transmit the appropriate energy.

Module 510F may generate and provide control signals for various processes such as, but not limited to, real-time imaging, and the coordination of timing of an intravenous injection of drug or other compound into a patient with the timing of transmission of ultrasound energy to a patient.

Peripheral controls and I/O module 510G may generate control signals that may be sent to external devices and peripherals that may be used in conjunction with ultrasound system 210. These devices and peripherals may include without limitation, an intravenous drug delivery system, transducer positioning systems, transducer position detecting systems, etc. I/O module 510G may also accept inputs from external devices and peripherals and provide them to other modules within control and computation block 510.

Control and Computation block 510 may also interface to user interface module 515. User interface module 515 may allow the use of one or more user interface devices such as, but not limited to, a keyboard, mouse, touch screen, trackball, touch pad, gesture-based interface, voice command interface, discrete switches or controls, and a display 520. Through the user interface, authorized users may operate ultrasound system 210. These operations may include the ability to choose the target region and to choose the subsets of elements 4156 to be used to generate ultrasound for treatment (if a manual control option is selected). Other operations may also be possible. In some embodiments selection of the target region is done by allowing a user to navigate a 3D rendered image using one or more of the user interface devices. Display 520 may be used to display various information including, but not limited to, the obtained ultrasound images, images from other modalities, merged images, patient information, and instructions or options for an authorized user.

For example, after having determined the subset(s) of transducer elements 415 that are to transmit ultrasonic energy, parameters may be set for a transmit operation. These parameters may include, but are not limited to, length of delays and transmission frequency. These parameters may be selected manually by the operator, or automatically based on a set of parameters, as discussed elsewhere herein. These parameters may be used and applied to various modules of ultrasound system 210.

During a transmit operation, system controls module 510F may send the appropriate control signals based on the parameters to transmit (TX) Amplifier 430. TX Amplifier 430 may then apply the appropriate signal to elements of ultrasound transducer assembly 220 either directly through multiplexer (MUX) 435 or through transmit/receive (TX/RX) switch 440 and then through MUX 435. In FIG. 5, TX amplifier 430 is shown to be coupled to MUX 435 by dotted line 525 and coupled to TX/RX switch by dashed line 530. This configuration enables the ultrasound system to drive transmit only elements in addition to the elements that are connected to both transmit and receive. The operation of different element types in this manner provides for certain advantages that are explained elsewhere herein.

In contrast, in conventional ultrasound imaging systems, a TX amplifier is typically only coupled to a TX/RX switch (with subsequent connections to the elements possibly through a MUX) and only support elements that can both transmit and receive. Thus, as dotted line 525 illustrates, TX amplifier 430 couples to MUX 435 which then couples via connection 225C to an example of a transmit only element 415B. Simultaneously, TX amplifier 430 may couple to TX/RX switch 440, which then couples through MUX 435 to connect through connection 225A to an example transmit and receive element 415A. Connection 525 from TX amplifier 430 to MUX 435 as shown in FIG. 5 is not present in conventional ultrasound imaging systems.

TX/RX switch 440 may serve to protect electronics in the receive path from relatively high voltages that may be present in the transmit path. Protection for elements that transmit and receive may be required as the electronics that transmit and the electronics that receive are electrically connected to the same physical transducer element. In the example embodiment shown in FIG. 5, the TX/RX switch 440 is not needed for transmit only element 4156 as element 4156 is not used for the receive operation.

In some embodiments, MUX 435 may be provided where the number of elements in ultrasound transducer assembly 220 is larger than the number of electronic channels within ultrasound system 210. With MUX 435, various subsets of elements in ultrasound transducer assembly 220 may be operated with the appropriate parameters even where there are fewer electronic channels than there are elements. It is anticipated that in practice, when utilizing these system and methods, that ultrasound transducer assembly 220 would have more elements of each kind (e.g. imaging elements 415A and treatment elements 415B) than channels capable of operating each kind.

For a receive operation, MUX 435 connects the elements that transmit and receive to the receive side electronics. The receive signal path is shown by the arrows going right starting from example transmit and receive element 415A. In this example embodiment, the signal passes through MUX 435, TX/RX switch 440, low noise amplifier (LNA) 445, time-gain compensator (TGC) 450, and analog to digital convert (ADC) 455. Signals digitized by ADC 455 may then be stored in storage module 510C for further processing by control and computation block 510.

FIG. 4, illustrates configuration of the general control subsystem of FIG. 5 for different transducer elements. Imaging element 415A is coupled to electronics 429A that enable transmit and receive operations as discussed above. TX amplifier 430A is coupled to TX/RX switch 440A which is then coupled to MUX 435A before coupling to element 415A through cable 225A, as shown by the dashed arrows. For receive operations, the ultrasound signal passes through MUX 435A, TX/RX switch 440A, LNA 445A, TGC 450A, and ADC 455A, as shown by solid arrows. The operation of both transmit and receive functions allows ultrasound imaging to be performed by ultrasound system 210. Electronics 429B is configured for another imaging element 415A opposite to the set described above. Electronics 429B may be the same as or similar to electronics 429A. The components included in electronics 429B are identified by references that include the suffix 'B'.

Element 415B is an example of an element that is configured to deliver ultrasound energy to facilitate treatment. In this example, element 415B is configured to only deliver ultrasound to target regions. Element 415B does not require electronics to enable it to receive echo signals. Therefore, element 415B is shown to be coupled to electronic components 429C that only enable transmit operations. Here, TX amplifier 430C is coupled directly to MUX 435C which is then coupled via cable 225C (illustrated by dotted arrows) to element 415B. A set of electronics 429D similar to electronics 429C is configured for another treatment element 415B. The components included in electronics 429D are identified by references that include the suffix 'D'.

Forming subsets of elements which may be configured so that all elements in a subset perform the same operation of either transmit only or transmit and receive may be advantageous. In FIG. 4, all elements within subsets 420A and 420B may be configured to transmit and receive, while all other elements, such as those in subsets 425A and 425B, may be configured to transmit only. An advantage that is offered by this approach is that certain subsets may be configured to optimally transmit and receive to form images, while other subsets may be configured to optimally only transmit to promote opening the blood-brain barrier. In some embodiments, the elements in the various subsets may be operated with different parameters such as, but not limited to, transmit frequency, and transmit bandwidth.

Elements in these various subsets may be designed differently and behave differently. Relatively higher ultrasound frequencies have been shown to experience lower amounts of attenuation and be effective for imaging certain portions of the brain. As such, in a non-limiting example, subsets of elements that form images may have a higher frequency response (e.g. centered at 2 MHz). In contrast, relatively lower ultrasound frequencies applied to the brain can selectively increase the permeability of the blood-brain barrier. As such, in a non-limiting example, subsets of elements used to deliver ultrasound energy to facilitate treatment may have a lower frequency response (e.g. centered at 0.5 MHz). In some implementations treatment elements are driven at frequencies in the range of 0.25 MHz to 5 MHz. In some implementations imaging transducer elements are driven at frequencies in a frequency range of about 1.75 MHz to 10 MHz.

In the example shown in FIG. 4 and in certain other example embodiments of this invention, the operation of one or more transducer elements that can transmit and receive, along with the operation of one or more transducer elements that can only transmit, is advantageous. Such configurations allow more transducer elements to be supported by fewer electronic circuits. As an example, transmit only elements require less electronics. Although it is desirable to have transmit only elements along with elements that transmit and receive, the systems and methods described herein do not preclude other configurations. In some embodiments, the same element can be operated in a "transmit only" mode, with one set of parameters when delivering ultrasound energy to facilitate treatment as well as in a "transmit and receive" mode, with another set of parameters when imaging.

Figure 6A:
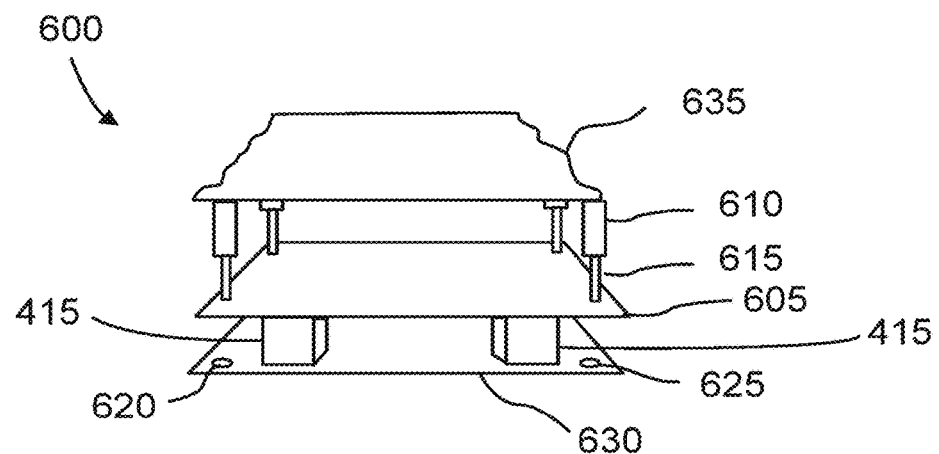
FIGS. 6A-6B are schematic illustrations showing example ultrasound transducer elements individually and coupled together.
Figure 6B:
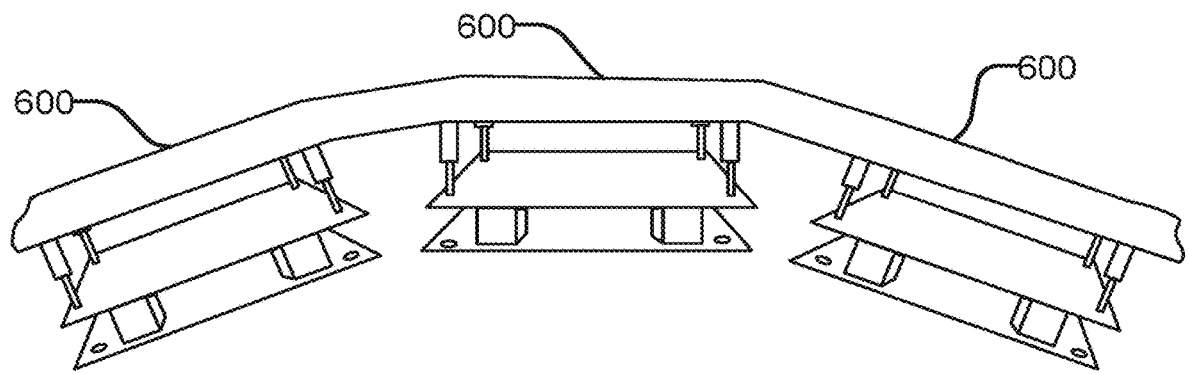

FIGS. 6A and 6B illustrate an example embodiment in which one or more elements are coupled to one or more sensors such as, but not limited to, angle sensors, pressure sensors, thermal sensors, proximity sensors, electroencephalogram (EEG) sensors, and slippage sensors. Such sensors may be provided optionally and beneficially in ultrasound transducer assembly 220.

In FIG. 6A, element group 600 comprises two ultrasonic elements 415, which are mounted on a common mechanical sub-structure 605. The orientation of mechanical substructure 605 may be controlled by any of various mechanisms. In this example embodiment, the orientation of mechanical sub-structure 605 is controlled by linear actuators comprising motors 610 (e.g. stepper motors, servo motors) or other linear actuators, only one of which is labelled for clarity. Each motor 610 may be coupled to a lead screw 615, only one of which is labelled, whose position may be controlled by a corresponding motor 610. Thus, by controlling the position of each lead screw 615 independently, the orientation of elements 415 may be controlled. Other implementations may use other types of linear actuators.

Sensors 620 and 625 are also shown. In the illustrated embodiment sensors 620 and 625 are embedded within cover 630, which may allow ultrasonic energy to pass through it. Cover 630 may also serve to separate the elements and skin, protecting each one from the other. In some embodiments, one or more of sensors 620 and 625 may be used to measure and report the orientation of the group of elements back to the ultrasound system. In these and other embodiments other sensed parameters may optionally be reported back to the ultrasound system. In this example embodiment, two sensors are shown, but more or fewer sensors may be provided.

FIG. 6A shows that the four motors 610 (e.g. stepper motors, servo motors or other rotary actuators) are coupled to mechanical structure 635. Mechanical structure 635 may provide the structure of ultrasound transducer assembly 220. FIG. 6B shows a case where three instances of element group 600 are coupled to mechanical structure 635, which forms or is a part of ultrasound transducer assembly 220. Electrical connections to the elements and the sensors are not illustrated in the figures for the sake of clarity. The spatial position of element group 600 within the structure of ultrasound transducer assembly 220 may be known to the ultrasound system from outputs of sensors attached to each element group 600 and/or from known locations of the transducer elements included in element group 600.

The capability to measure and control the orientation of elements within ultrasound transducer assembly 220 is advantageous as it facilitates orienting elements in desired configurations, such as normal or nearly normal to the surface of the skull. This orientation is known to reduce or remove the possibility of mode conversion between longitudinal and shear waves at the surface of the skull. In some embodiments, the orientation of elements may be adjusted automatically. A pre-op image may be used to assess the angularity of the skull (e.g. by determining a tangent plane) at any location, and through the process of registration, as discussed herein the angularity of any section of the skull may be known. An element may thus be automatically adjusted to be oriented at a desired angle with respect to the skull using this knowledge.

This capability is also advantageous because it permits ultrasound transducer assembly 220 to accommodate differently shaped heads. In some embodiments, motor 610 may advance or retract one or more lead screws 615 to position one or more ultrasound elements 415 or element groups 600 such that ultrasound transducer assembly 220 conforms to the shape of a patient's head. It will be appreciated that motor 610 can be any type of linear actuator operable to advance or retract element(s) 415, such as a stepper or servo motor.

Robotically Positioned Transducers

Figure 7A:
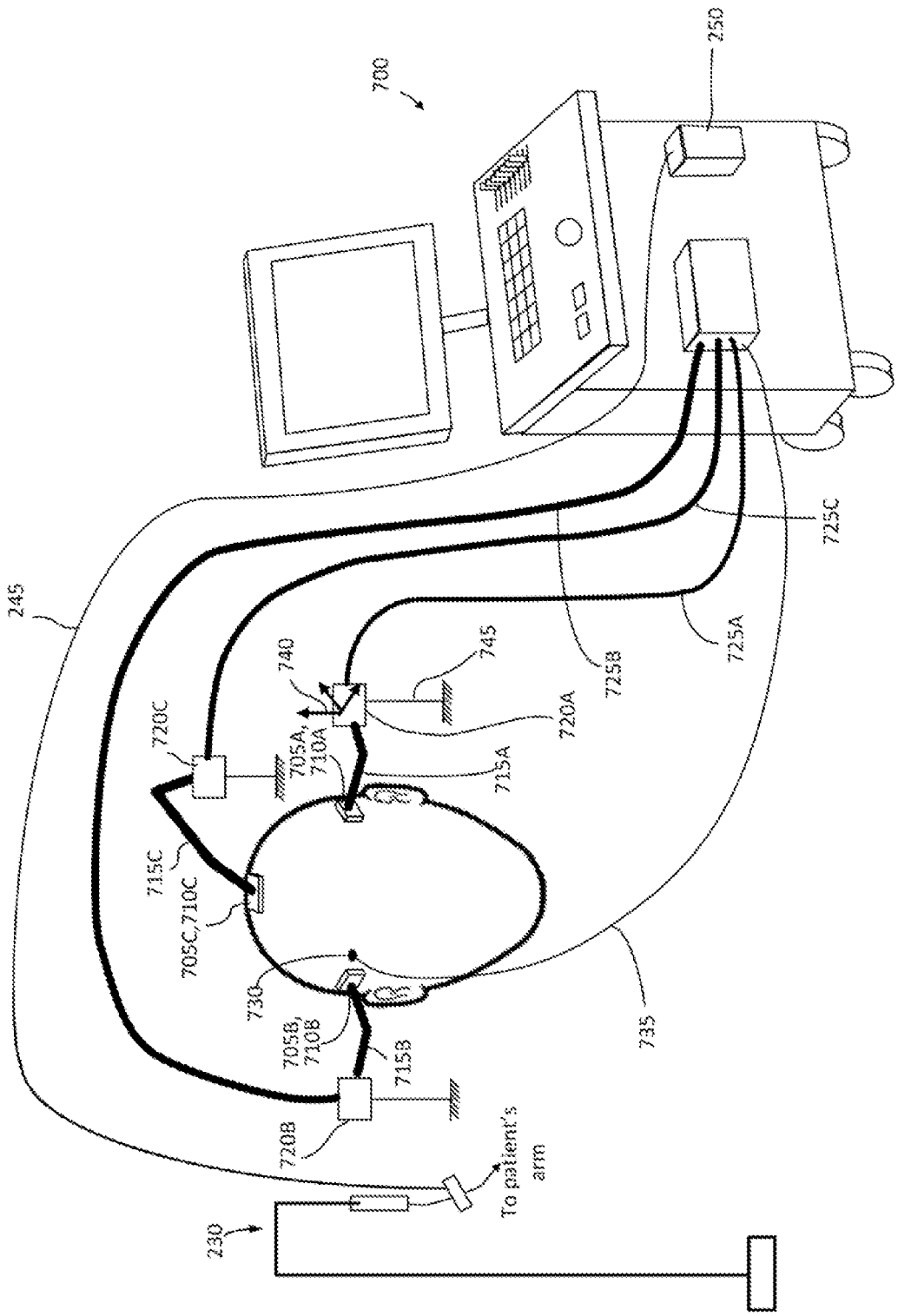
FIG. 7A is a schematic illustration showing an example ultrasound system that includes robotic arms operable to position ultrasound transducers.

FIG. 7A shows an ultrasound system 700 according to an example embodiment which features a robotic manipulator (in this example provided by electromechanical arms). In system 700, ultrasonic elements are in element housings 705A, 705B and 705C (any individual element housing herein referred to as element housing 705, or collectively as element housings 705). Element housing 705 and the elements contained within it may collectively be called a transducer 710 (e.g., 710A, 710B, 710C).

Each transducer 710 can include one or more transducer elements. The elements can be arranged in any of various configurations such as, but not limited to, linear, in a 2D array format, randomly distributed, in a plane, in a 1D convex or concave shape or in a 2D convex or concave shape. The elements may be built on a structure that makes it possible to attain flexible shapes of the surface of the elements. One benefit of such a capability is that it may be possible to match or closely match the surface of the skull over the region of a footprint of the housing that is in contact with the skull. This capability may be achieved, for example, with mechanisms as shown in FIGS. 6A and 6B. Transducer 710 may comprise one or more element groups 600, and may implement methods for positioning the elements as described above.

Elements supported by element housing 705 may all be capable of transmitting and receiving, or may only be connected for transmitting. It is also possible for both types of elements to be present within element housing 705.

Each transducer 710 may be coupled to an electromechanical arm 715 or other movable support that is capable of positioning the corresponding housing 705 in one or more degrees-of-freedom (DOFs). In some embodiments, arms 715 are capable of positioning the corresponding transducers 710 in 6 DOFs. Arms 715A, 715B, and 715C (any individual arm herein referred to as arm 715, or collectively as arms 715). It is to be noted that although three arms are illustrated, configurations with more or fewer arms 715 are possible. In addition to being able to position transducer 710, arm 715 may support electrical cables or other pipes or lumens. The pipes or lumens may carry fluids such as, but not limited to, ultrasound coupling gel. In some embodiments the pipes or lumens are arranged to dispense ultrasound coupling gel at the interface between a transduce 710 and a patient. The electrical cables, pipes, or lumens may, for example, be carried in a conduit that extends along an arm 715. In some embodiments, the conduit is located within arm 715.

The position and orientation of each arm 715 may be manually or robotically adjusted. In a non-limiting example, inverse kinematics may be used to determine the angle of each joint of a mechanical arm to achieve a desired position for transducer 710. Arms 715A, 715B, and 715C are shown to be coupled to arm control units 720A, 720B, and 720C respectively (any individual arm control unit herein referred to as arm control unit 720, or collectively as arm control units 720). Arm control units 720 may contain electrical or electromechanical systems operable to control the orientations and positions of arms 715. The details of such electromechanical systems are generally well known and are therefore not provided here.

Control signals that control the position and orientation of arms 715 may originate from peripheral controls and I/O module 510G and be sent from ultrasound system 700 to each arm control unit 720. Cables that carry these control signals are illustrated by the dashed lines labeled 725A, 725B and 725C. It will be appreciated that several cabling and electronic configurations are possible, and FIG. 7A shows a non-limiting example. In one example embodiment, MUX 435 shown in FIG. 5 may be physically placed in ultrasound system 700. In another example embodiment, MUX 435 may be placed within an arm control unit 720.

Each arm control unit 720 may be coupled to a mechanical ground such as, but not limited to, a free-standing support structure, railing of beds, and support structures coupled to chemotherapy chairs. The use of a mechanical ground may help provide support such that the position and orientation of arms 715 may be controlled. Just as in FIG. 2, ultrasound system 700 may also be coupled to an electronically controlled IV drug delivery system 230.

Sensors of many types may be associated with ultrasound transducers. For example, such sensors may include one or more of:
one or more pressure sensors which measure forces between a transducer and a patient;
one or more position sensors;
one or more electroencephalography sensors (EEG) to measure electrical activity of the brain;
etc.

The construction of such sensors and how they may be attached to transducers is explained in further detail with reference to FIG. 8.

Information collected from sensors may be sent via cables 725A, 725B, and 725C to control and computation block 510. Parameters such as, but not limited to, ultrasound parameters (gain, frequency, etc.), or control signals to control the position of arms 715 may be generated in response to the received sensor information.

In an example embodiment, a contact angle sensor in contact with the patient's skull is coupled to a transducer 710. The sensor may report the angle of the head at the skull at the point of contact to computation block 510, which allows peripheral controls and I/O module 510G to generate control signals. These control signals may be sent to arm control unit 720C and may comprise the commands necessary for arm control unit 720C to execute the commands and move arm 715C in such a way that element housing 705C is oriented at the desired position and angle relative to the skull.

In some embodiments, once positioned at the desired configuration, arms 715 may automatically reposition themselves if the patient moves. This automatic repositioning may include repositioning element housings 705 such that the same region of the brain may be insonated or imaged regardless of the motion of the patient.

Ultrasound system 700 may be programmed such that if the target area or volume being insonated or imaged is different by a certain threshold then certain actions are triggered. In a non-limiting example, this threshold is triggered when a threshold proportion or amount (e.g. 1%) of the target area or volume is different from a reference target area or volume. In some example embodiments, ultrasound images are obtained as described herein periodically or continuously and all or some features of a current ultrasound image are compared to corresponding features of a previous ultrasound image. An action may be triggered if a value of a metric indicative of differences between the current and previously acquired ultrasound image crosses a threshold.

The action(s) that are triggered may include, but are not limited to, stopping the imaging or treatment session, automatically trying to reposition transducer 710 so that the same area is addressed (within a threshold), or asking for an authorized human operator to intervene to manually reposition transducer 710 (e.g. by pausing the session and providing instructions to the operator through a user interface).

Ultrasound system 700 may include the capability of adjusting each arm 715 independently of the other arms 715. Alternatively, arms 715 may be automatically positioned in concert with one another, given information on the shape of the patient's head and its motion.

In some embodiments, information about the patient's movements may not be limited to those provided by the sensors within element housings 705. Sensors such as, but not limited to, cameras may also be placed in other locations such as the bed, ceiling, the patient, and other freestanding structures. Such sensors may be used to supply information on patient motion. Camera based position tracking systems are commercially available and may be applied to track position(s) and orientations of transducer(s) 710 and/or the patient's head.

FIG. 7A shows inertial measurement unit (IMU) sensor 730 placed on the patient's head. The reading from this sensor may be sent via cable 735 to ultrasound system 700 to be processed by peripheral controls and I/O module 510G. If the reading of the patient motion exceeds a threshold value, module 510G may calculate new positions for arms 715.

Calculations regarding change in patient position may be performed continually or on a periodic basis, depending on how ultrasound system 700 is configured. In an example calculation, an initial position of the patient's head, is obtained and stored along with the position and orientation of a transducer 710. Assuming that transducer 710 is initially at an appropriate location for the function it is configured to perform, any movement of the patient may be recorded. Thus, any change in position of transducer 710 relative to the patient may trigger a calculation to determine whether a current location of transducer 710 is still within a threshold of the appropriate target volume. If a threshold is exceeded, then control signals may be sent to arm control units 720 to reposition element housings 705 to target the desired volume. Actions other than updating the position of element housings 705 may also be programmed to take place. In an example embodiment, if the threshold is exceeded by a certain amount, actions such as stopping scanning, or providing warning messages may be performed by ultrasound system 700.

Ultrasound system 700 may provide certain advantages over ultrasound system 210 in some scenarios. For example, ultrasound system 700 may require fewer transducer elements for operation, as transducer elements may be dynamically positioned during treatment. Furthermore, variations in patients' anatomy, namely head size and shape, can make fabrication of an ultrasound transducer assembly 220 suitable for use with a range of patients difficult.

Manually Positioned Transducers

Figure 7B:
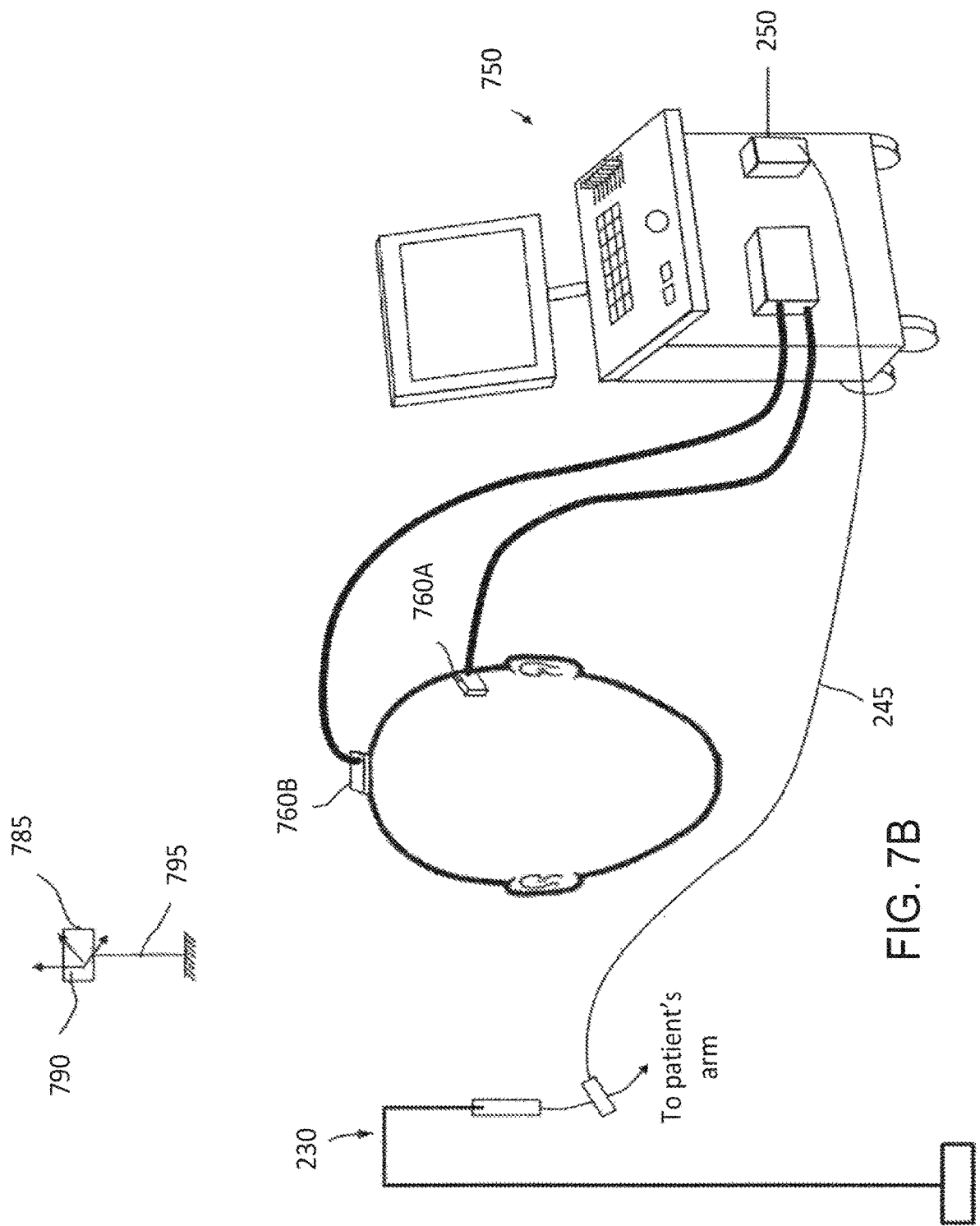
FIG. 7B is a schematic illustration showing an example ultrasound system with transducers that are manually placed.

FIG. 7B illustrates an ultrasound system 750 having yet another configuration. Ultrasound system 750 is similar to ultrasound system 700 and also comprises one or more transducers which may image and/or deliver ultrasound energy to facilitate treatment. In system 750 one or more, ultrasound transducers may be placed at appropriate positions on a patient's head manually by a person. In some embodiments, 6 DOF sensors may be coupled to transducers 760A and 760B. Such sensors may allow for the positions and orientations of transducers 760A and 760B to be tracked and communicated to ultrasound system 750. Although not illustrated, patient movements may be monitored in this configuration just as described in FIG. 7A. In other embodiments, a single transducer may be provided which an operator could appropriately place in one or more positions to both perform imaging and facilitate treatment.

Sensors such as position or pressure sensors may be used beneficially with ultrasound system 750. As an illustrative example, providing position sensors on transducer 760B would allow ultrasound system 750 to compare the actual location of transducer 760B to a desired location. This would allow for further feedback and instructions to be provided to a user to adjust its position.

Figure 8:
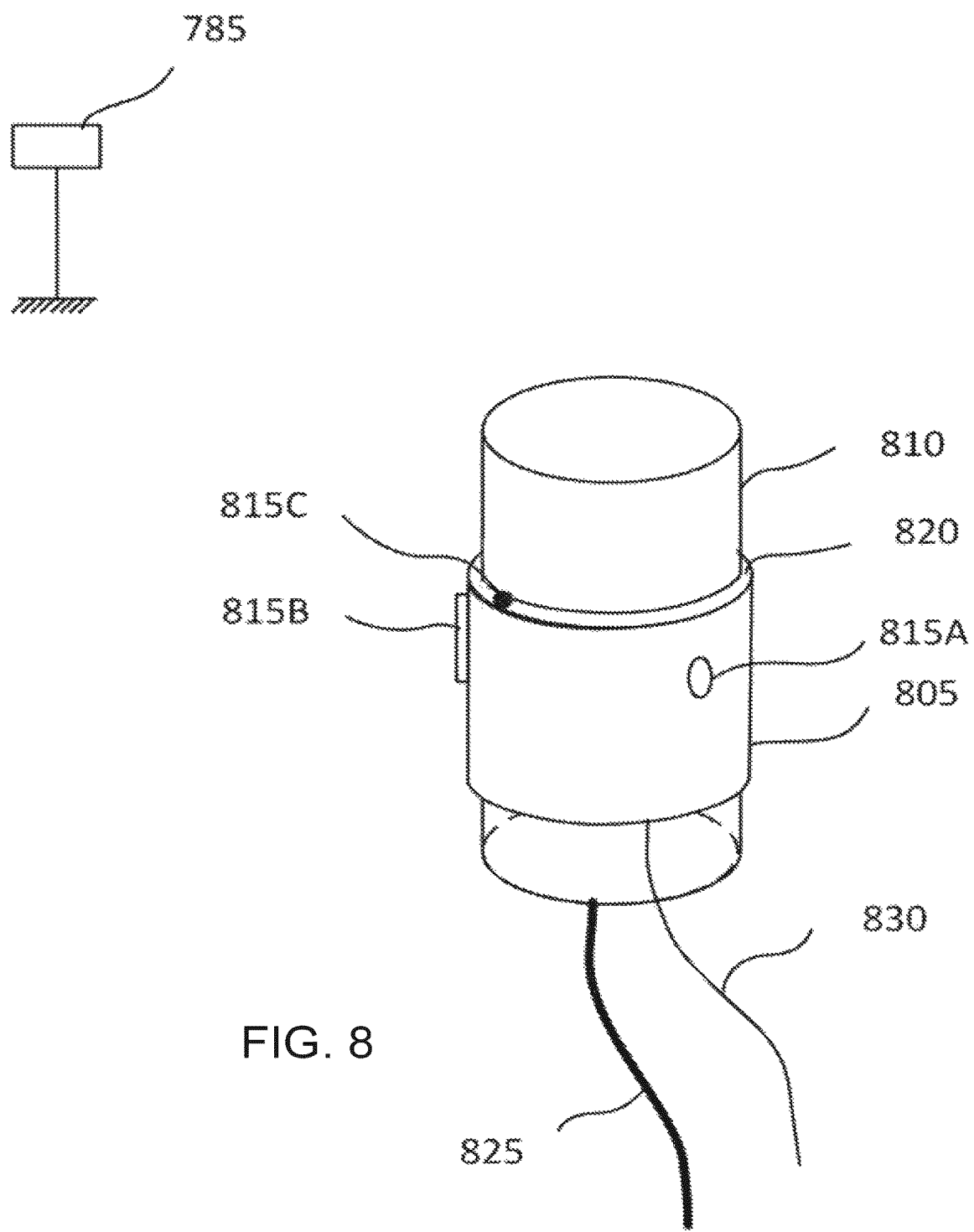
FIG. 8 is a schematic illustration showing an example arrangement for coupling one or more sensors to a transducer.

FIG. 8 shows an example construction for coupling one or more sensors to a transducer. In this example, rigid sleeve 805 fits tightly over transducer 810. Sleeve 805 supports one or more sensors. Sensors 815A, 815B, and 815C (any individual sensor herein referred to as sensor 815, or collectively as sensors 815) may be placed on sleeve 805 as pictured, or wherever else appropriate. The rigidity of sleeve 805 allows transducer 810 and sensors 815 to remain stationary relative to each other once sleeve 805 is fitted over transducer 810. In this example embodiment, sleeve face 820 is not level with the surface of transducer 810. However, the two faces may be in the same plane in other embodiments.

A sensor, such as sensor 815C, may be a pressure sensor, measuring the pressure with which the transducer presses against the skin of a patient. As shown, transducer 810 may be electrically connected to transducer cable 825. Similarly, sensors 815 may be connected to sensor cable 830. In the present example, sensor 815C may output pressure data through sensor cable 830 to ultrasound system 700 or 750, which may then be received by control and computation block 510.

Modules within control and computation block 510 may compare the received pressure data to a range of desired pressures. The data on the range of desired pressures may be stored in storage module 510C. If the received pressure data falls outside the desired range, certain actions may be triggered. These actions include, but are not limited to, showing a warning through user interface 515, and if transducer 810 is coupled to an electromechanical arm 715 such as one shown in FIG. 7A, controls may be sent to arm control unit 720 to alter the position of transducer 810 to obtain a pressure within the desire range.

Establishing a Common Frame of Reference

It may be advantageous to establish a common frame of reference to describe measurements of location and orientation of the various sensors in a common coordinate system. A common frame of reference is a convenient but arbitrarily chosen coordinate system having an origin and orientation to which all images and locations can be referred. For example, in the configuration illustrated in FIG. 7A, a coordinate system 740 may be located relative to arm control unit 720A. This coordinate system may then be used as a frame of reference for all other position and orientation related measurements (the "common frame of reference"). In the configuration illustrated in FIG. 7B, coordinate system 790 may be used to establish the common frame of reference. In both of these examples, an origin of the frame of reference is located at a mechanical grounds (745 and 795, respectively). The frame of reference in the configuration shown in FIG. 4 is represented by coordinate system 460. This frame of reference is different from the ones shown in FIGS. 7A and 7B in that it is not mechanically grounded. Coordinate system 460 can move if the patient moves his or her head. However under the assumption that ultrasound transducer assembly 220 and head 410 are not moving relative to each other, this type of frame of reference is equally valid and appropriate and results in no additional computational complexity.

Some implementations provide systems and methods for establishing a common frame of reference using a position sensing system. Various types of position sensing systems may be utilized such as, but not limited to, electromagnetic (EM) based system or optical based systems.

FIGS. 7B and 8 show an example embodiment which uses an EM transmitter 785 to determine positions of sensors associated with ultrasound transducers. For example, EM sensors may be placed on sleeve 805 and reference EM transmitter 785 may be able to establish the transducer's position and orientation in a coordinate system defined relative to reference EM signal generator 785. Thus, if multiple transducers were present (as shown in FIG. 7B), and each transducer is coupled to one or more EM sensors, the position and orientation of each of the transducers may be found in relation to the frame of reference, and subsequently, in relation to each other. Knowledge of the position(s) and orientation(s) of transducers may be used optionally and beneficially with the methods of placing transducers in an appropriate location as discussed above.

Obtaining Ultrasound Images

Returning to example method 300 in FIG. 3, after pre-op MRI or CT images of the head are obtained and imported into an ultrasound system in step 305, real time imaging of at least a portion of the patient's head is performed in step 310. It is desirable to obtain an image of parts of the patient's brain which include certain structures within the brain. As described previously, certain structures may be imaged through low attenuation acoustic windows using ultrasound. As such, in some embodiments, ultrasound transducers used to form images may be positioned at these low attenuation acoustic windows. Ultrasound imaging may then be performed, and structures visible in these images may be selected to serve as the ultrasound image reference region. The process of selection may be accomplished by segmentation as explained below.

To illustrate how this may be performed with the configuration in FIG. 4, ultrasound transducer assembly 220 may be positioned on patient P's head such that subsets 420A and/or 420B are adjacent to patient P's temples. Using the knowledge about the general anatomy of the skull, ultrasound transducer assembly 220 may be constructed such that when a patient wears the assembly, subsets configured to image are positioned adjacent to one or more low attenuation acoustic windows.

In the configuration shown in FIG. 7A, instructions may be provided by ultrasound system 700 to control arms 715 such that imaging transducer 710A and/or 710B are positioned adjacent to low attenuation acoustic windows.

In the configuration shown in FIG. 7B, a human operator may manually position transducer 760A such that it is placed appropriately at one of these windows. Sensors on transducer 760A may detect whether the desired location has been reached and may give feedback to the operator if adjustments are required.

Reference Region Selection

In step 315, the image of the structure seen in the ultrasound image reference region obtained in step 310 may be identified in the pre-op MR or CT scan. As an example, this may involve a human operator selecting this structure in a slice of the pre-op image dataset or in a 3D model constructed from the pre-op image dataset. Again, this selection may be accomplished by segmentation. The region in both the pre-op image(s) and the ultrasound image containing the common structure will be collectively referred to as "reference regions". In some embodiments, reference regions may comprise one or more of the following structures: the circle of Willis, ventricles, and/or the corpus callosum. Utilizing the common structure identified in step 315, the images of the ultrasound scan can be registered to the pre-op MRI or CT scan in step 320.

Registration

The registration process may use one or more features of the reference regions. As an example, registration may be performed by matching the shape of the reference region in both the ultrasound and the pre-op modality. Other characteristics may be used, such as the orientation of the reference region relative to an expected orientation, or if two or more reference regions exist, the relative orientation of the two or more reference regions etc. As an example, the circle of Willis typically has a distinctive shape that generally appears as an irregular hexagon or a rough circle in an ultrasound image. However, regardless of the shape, because the same anatomy is imaged by the two modalities, a strong correlation may exist between the images of the reference regions in the two modalities.

Figure 9:
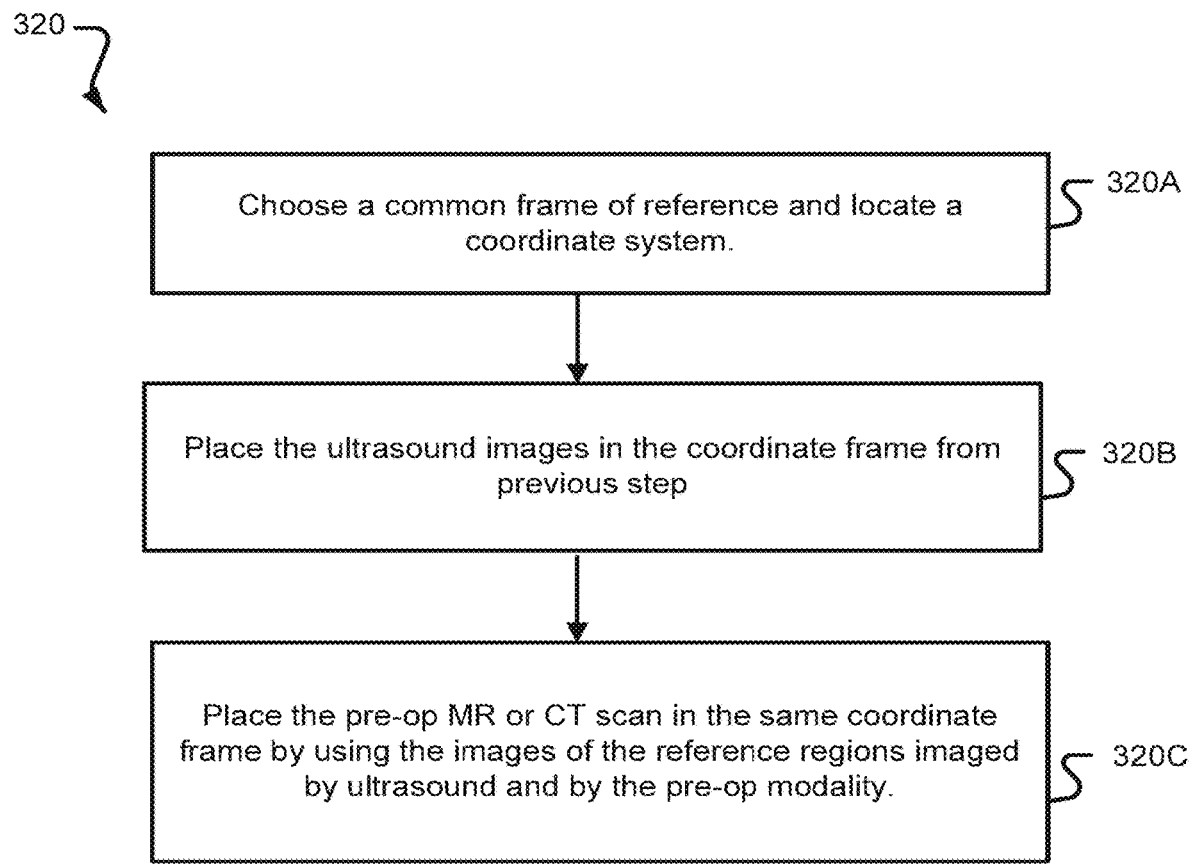
FIG. 9 is a flow chart for an example method for registering pre-operation images with ultrasound images.

FIG. 9 illustrates an example method for accomplishing the registration in step 320. At step 320A, a common frame of reference may be chosen by establishing a coordinate system as described above. In step 320B, the structures of the ultrasound images may be located within the selected coordinate system. The distance of the imaged structure from the transducer may be calculated based on the travel time of ultrasound echoes and the location and orientation of the transducer are known, which allows for step 320B to be accomplished. Step 320C involves placing the pre-op MR or CT scan in the coordinate frame by using the same reference regions present in the ultrasound and the pre-op images.

Figure 10:
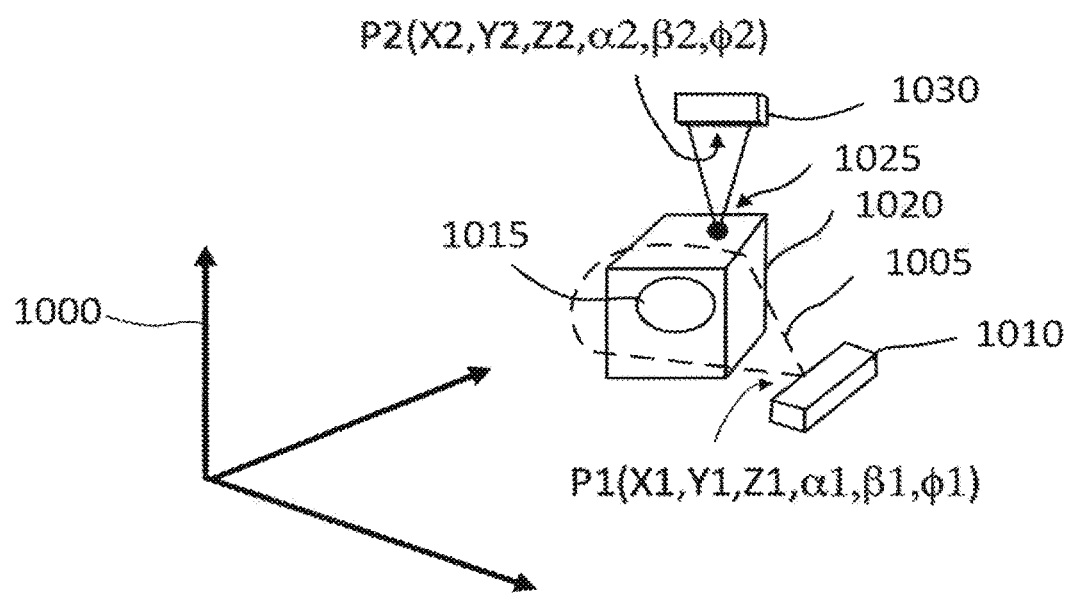
FIG. 10 is a schematic illustration showing an example registration process.

FIG. 10 illustrates an example registration process. Coordinate system 1000 may be selected in step 320A. Coordinate system 1000 may be arbitrarily chosen to be coupled to a mechanical ground, such as arm control unit 720A. Ultrasound image 1005 is represented by dashed lines at a location and orientation relative to imaging transducer 1010. This serves to illustrate the relationship between ultrasound image 1005 and imaging transducer 1010 that created the image. As shown, $P1(X1,Y1,Z1,\alpha1,\beta1,\phi1)$ may represent the location and orientation of the origin of ultrasound image 1005 and may also represent location and orientation of the center of imaging transducer 1010's face of transducer elements. Variables x, y and z may indicate the coordinates within coordinate system 1000 while variables $\alpha$, $\beta$, and $\phi$ may indicate the roll, pitch and yaw within coordinate system 1000. Step 320B may then be completed by placing ultrasound image 1005 within coordinate system 1000, with its origin at $P1(X1,Y1,Z1,\alpha1,\beta1,\phi1)$. The variables $X1, Y1, Z1, \alpha1, \beta1, \phi1$ may be known from outputs of sensors such as EM sensors of an EM position sensing system that are coupled to the transducer and the accompanying EM transmitter.

Although FIG. 10 illustrates the use of a transducer (e.g. as an element housing and the elements contained within), other configurations are not excluded. For example, these methods may be performed with ultrasound transducer assembly 220 as pictured in FIG. 4, where imaging transducer 1010 may comprise several elements, or subsets of elements, together configured to form images (e.g. subset 420A).

A reference region, pictured by 1015 in FIG. 10, such as the circle of Willis, may be imaged by imaging transducer 1010 through a low attenuation acoustic window. Step 320C of method 320 may be performed in this example embodiment by placing the pre-op images, represented by the volume 1020, within coordinate system 1000. Software for registration step 320C may be implemented utilizing registration module 510E.

Figure 11:
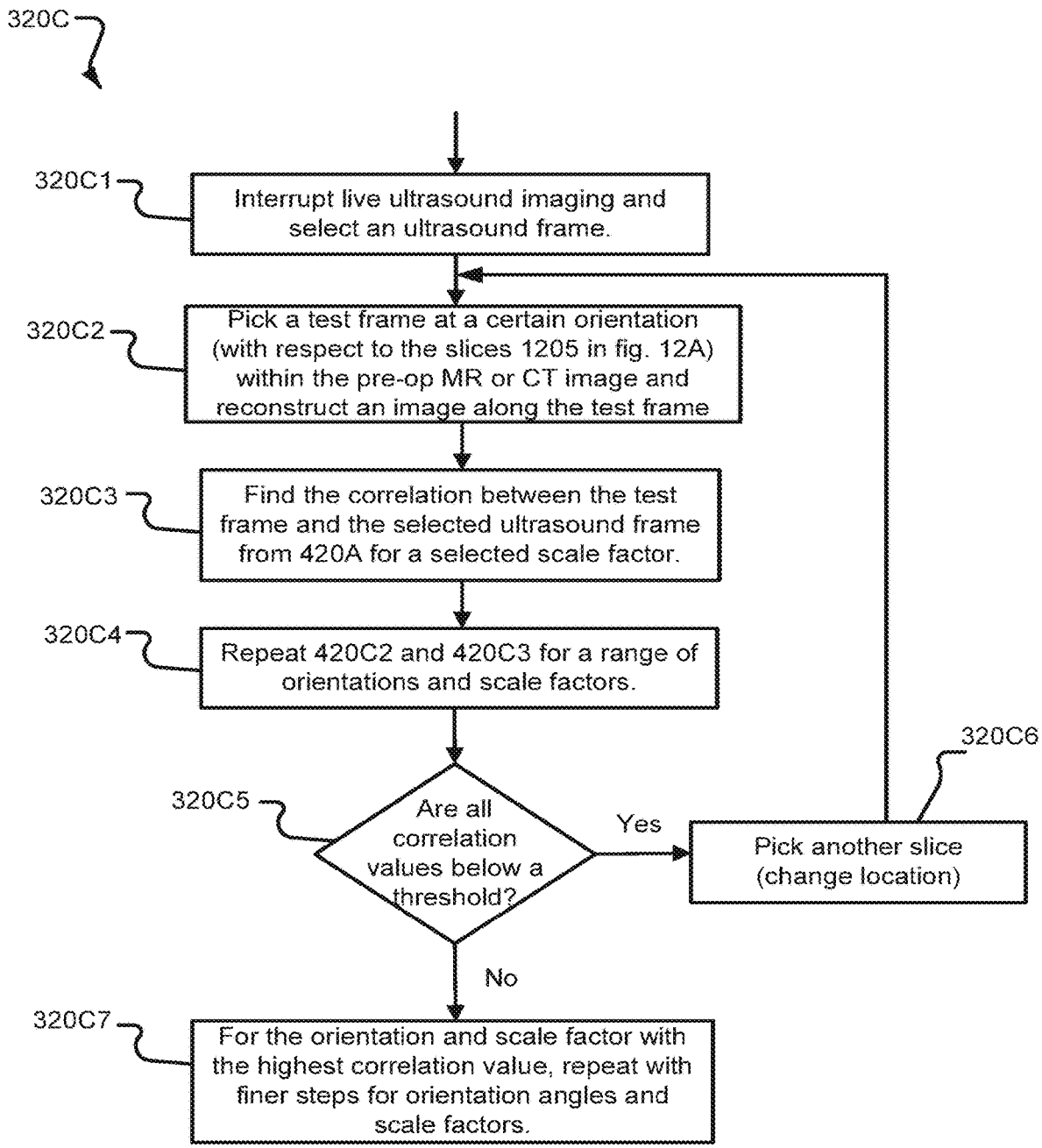
FIG. 11 is a flow chart for an example method for registering pre-operation images with ultrasound images.

FIG. 11 is a flow chart illustrating an example method which includes further actions that may be taken to perform step 320C to place pre-op images into the reference coordinate system. At step 320C1, assuming that live imaging of the patient is being performed with an ultrasound imaging system, the live ultrasound imaging may be stopped and an appropriate frame containing the image of the reference region is selected. Following this, it is desirable to find an appropriate slice within the pre-op images that best corresponds to the image of the reference region in the selected ultrasound frame is selected.

Figure 12A:
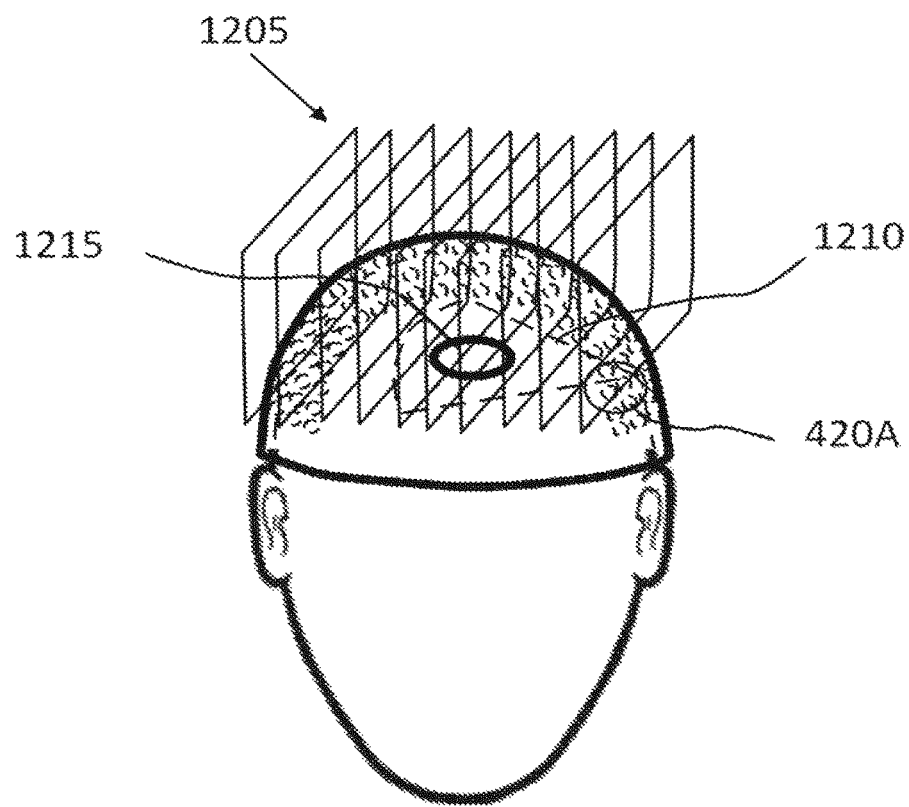
FIGS. 12A-12B are illustrations of how the registration process may be performed.
Figure 12B:
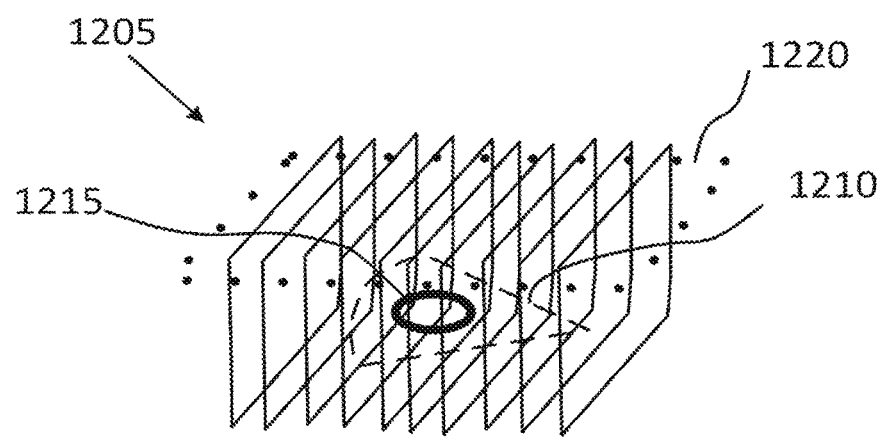

FIGS. 12A and 12B illustrate an example registration process using a reference region. Slices 1205 through the skull depict one set of slices through the image data set acquired by the pre-op modality. For reference, slices 1205 may represent volume 1020 in FIG. 10. Dashed lines 1210 represent the boundary of an ultrasound image and may correspond to ultrasound image 1020 in FIG. 10. It should be noted that other slices of the pre-op images and other orientations of the ultrasound plane may be obtained, and the example shown is only one possible configuration. Reference region 1215 is represented in this example by an oval in the patient's brain, and may correspond to 1015 in FIG. 10.

At step 320C2 of method 320C, an initial test frame is selected in the pre-op image(s) that closely matches the ultrasound image. An example of such a test frame is illustrated by plane 1220 in FIG. 12B (shown in bold dotted lines). The selection of plane 1220 may be performed automatically or may be guided by a human. An image may be reconstructed along plane 1220 from the pre-op image data contained in slices 1205. In FIG. 12B, the image that is constructed would be in a plane substantially normal to slices 1205. However, it is noted that test frames that provide for a constructed image in any number of orientations relative to slices 1205 may be selected.

Method 320C continues to step 320C3 where the correlation between the image produced in step 320C2 and the ultrasound image frame along plane 1210 produced in step 320C1 is found. In step 320C4, the correlation between the selected ultrasound image and the reconstructed image along the selected slices 1205 is found for a range of orientation angles of the test frame and scale factors. This process may be carried out automatically by a computer, but may also be guided by a human in order to converge on a solution in a more expedient manner. After a desired number of permutations of the various transformations are computed, method 320C continues to decision block 320C5. If all of the correlation values are below a desired threshold, method 320C continues to step 320C6 where the location of plane 1220 is modified, and steps 320C2-320C5 are repeated. Conversely, if the correlation values for any of the calculations are above a desired threshold, decision block 320C5 continues to step 320C7. Step 320C7 attempts to find a slice with an even higher correlation value.

Using the example method 320C allows for a "best fit" slice to be found. A best-fit slice may be described as a slice of the pre-op images that shows the same structures as seen by the ultrasound image in the same plane and lies closest to the ultrasound image plane. For example, in FIG. 12B, the best-fit slice lies along ultrasound plane 1210. Having completed the registration process in method 300 and obtained the best-fit slice, images from the pre-op imaging modality may be located within the reference coordinate system alongside presently obtained ultrasound images. Because the coordinates of the ultrasound image's reference region is known within the coordinate system, the best-fit slice in the pre-op images may be assigned these same coordinates. The coordinates of a region identified in one modality can now be found in the other modality. This allows for a target target region identified in the pre-op modality to be located in the ultrasound image and common coordinate system.

In the process of alignment in step 320C, operations such as scaling, rotation and transformation may be performed on the pre-op images. The need for these operations may arise due to the nature of the imaging modalities and how the images are acquired. It is also possible that these operations are done on a section by section basis (i.e. each image may be broken down into different sections and a different set of operations may be used on each section). In a non-limiting example to illustrate how scaling may be performed, the selected ultrasound frame in step 320C1 and the test frame from the pre-op modality in step 320C2 may contain a different number of pixels. 1 $cm^2$ in the ultrasound system may contain 50 pixels, while 1 $cm^2$ in an MR image may contain 60 pixels. In this example, the MR image may be downsampled such that both images have the same pixel density. In other embodiments, the ultrasound image may be upsampled or downsampled to conform to a pre-op image's pixel density.

In some embodiments, ultrasound images and pre-op images may be processed. Processing may include, but is not limited to, image smoothing, speckle reduction, and edge detection. This processing may be performed optionally but beneficially prior to or during registration step 320. Performing these steps to improve image quality may improve the ability to find a best-fit slice. Individual characteristics from each imaging modality may be reduced or removed such that the images from the various modalities may be better compared or utilized in algorithms, for example, to find correlations.

In some embodiments, the registration step is carried out plural times using ultrasound images obtained from different low attenuation acoustic windows. Example embodiments of this invention have thus far shown ultrasound transducers or transducer elements situated at the temples to perform imaging. However, the skull is also thinner in areas such as the behind the eyes and in the back of the head, resulting in lower ultrasound attenuation allowing certain brain structures to be imaged by ultrasound. This may be accomplished, for example, by using transducer elements on ultrasound transducer assembly 220 that are located in the back of the head in the configuration shown in FIG. 4, or by positing a transducer in the back of the head in the configuration shown in FIG. 7A. By repeating the registration procedure using different ultrasound images, the accuracy of registration may be improved by selecting the ultrasound image/pre-op image pair that produces the highest correlation values.

Selection of Target Regions

At any point in method 300 after pre-op images are obtained in step 305 and before the configuration of subsets and transducers to be used are determined in step 330, one or more regions may be selected by a physician in the pre-op image(s) for ultrasound energy to be delivered in step 325 (defined as "target regions" above). In FIG. 10, one such target region is represented by a black dot 1025. Through the process of registration, the location of target region 1025 once it has been selected, is known within coordinate system 1000. Once registration in step 320 has occurred, the coordinates of the target region may be known, and this may be provided to one of the various ultrasound system configurations discussed herein. It may be advantageous to select target regions prior to beginning treatment of the patient in some scenarios. For example, a physician could perform this step prior to treatment. Without the time constraints that exist while treating a patient, more careful consideration of the target region(s) could result in better outcomes.

Calculation of Delivery Subset

In step 330 of method 300, depending on the configuration of the ultrasound system, calculations are made to either find the subset of elements or to find the position and orientation of a transducer (either may be referred to as a delivery subset) that may be utilized to deliver ultrasound energy to the target region(s). The goal in doing so is to allow ultrasound to be delivered to one or more locations at which it is desired to promote the opening of the blood-brain barrier to allow drugs to enter brain tissue. These calculations may be used, for example, to determine where a second transducer, such as transducer 1030 in FIG. 10, should be positioned in order to insonate the target region. In this example, if the calculations result in a position and orientation $P2(X2,Y2,Z2,\alpha2,\beta2,\phi2)$ within reference coordinate system 1000, transducer 1030 may be placed at P2 in order to insonate target region 1025.

In some embodiments, a number of factors may be taken into account in performing the calculations mentioned above. Relevant factors include, but are not limited to, distance between the target region and the transducer elements, attenuation of intervening tissue, orientation of the skull, and frequency characteristics of the transducer elements. Additionally, certain goals may be assigned. Example goals may include selecting a delivery subset that can open the blood-brain barrier to allow drugs to be delivered with the least amount of acoustic power, or in another example, in the shortest amount of time given a specific acoustic power setting. These factors may influence the calculations in different ways, and may individually interact with one another. For example, choosing a subset that is closest to the target region may not always be the optimal choice. The shape of the skull adjacent to these subsets may be such that it is at an angle to the plane containing the target region that results in significant mode conversion. As a result, sufficient energy may not be deposited at the target regions. In this example, it may be more desirable to select a subset that is farther away from the target region, but where less mode conversion will occur.

In some embodiments, the distance between a target region and the delivery subset may be calculated using the pre-op images. Because the pre-op images are registered within the common frame of reference which includes the position of each element (regardless of its use for imaging or for facilitating treatment) and the location of the target region, the intervening distance may be easily obtained.

In some embodiments, the attenuation of intervening tissue at a certain point on the surface of the patient's head may be calculated using the pre-op images. Analysis of the pre-op images may reveal different layers of tissue between transducer elements and the target region. By segmenting these layers either automatically or manually, each layer may be associated with attenuation parameters based on a priori data. Thus, it is possible to know the attenuation that may be experienced for different delivery subset positions. This information may be applied to influence the choice of the delivery subset and/or to set amplitude or other transmit parameters.

3D Model Generation

A 3D computerized model of the patient's head may be generated by the ultrasound system within head model generation module 510H. This model may be generated based on the registered pre-op images within the common frame of reference. Patient head movement during treatment helps to illustrate a useful aspect of this concept. When patient head movement occurs, the movement can be tracked by various sensors as described elsewhere herein. The location of the model within the frame of reference may be recalculated to reflect the new position within the reference coordinate system. This provides an advantage of not having to perform the registration steps 320 every time the position of the patient's head is changed.

The head model may have various degrees of sophistication. For example, the 3D model may only include the outline of the skull corresponding to the outermost layer of the skin. A more sophisticated example 3D model may include the outline of the skull and the thickness of the skull. An even more sophisticated example 3D model may include the various layers of the brain, including estimations of sound velocity in the various layers of brain tissue. The use of a computerized model is beneficial because it facilitates calculations and transformations, examples of which are discussed below.

Figure 13:
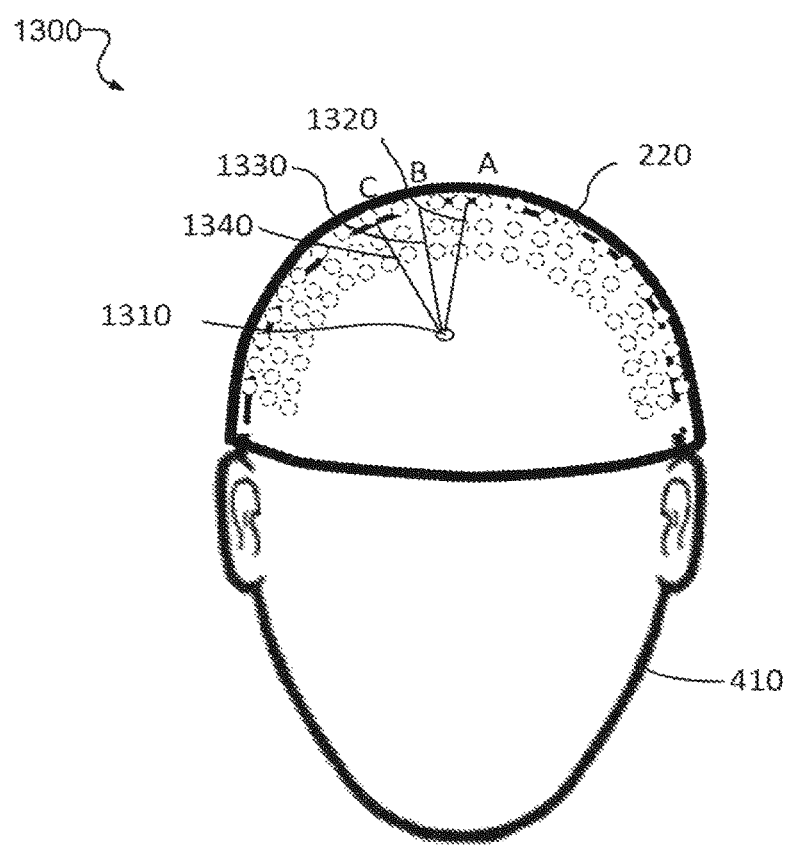
FIG. 13 is a schematic illustration showing an example method for determining the distance from the surface of the skull to a target region.

FIG. 13 illustrates an example application of a head model in determining delivery subsets. A simple model 1300 may include information about the outermost layer of head 410. Within this model, the location of target region 1310 may be known. In this non-limiting example of a calculation for the selection of a treatment subset, the distance from a region on the outermost layer of the skull to target region 1310 is the only factor taken into account. Distances from regions A, B and C on the surface of the head to target region 1310 are indicated by lines 1320, 1330, and 1340, respectively. In this example, region B has the shortest distance and thus, a subset of elements around region B may be chosen as the treatment subset.

In some embodiments, the computation of which region on the surface of the head has the shortest distance to target region 1310 may be performed by computation of transmit subsets and transmit parameters module 510A. Each said region in this example embodiment may comprise one or more transducer elements.

An example embodiment of the calculation of the size of the treatment subset of transducer elements is now provided. In a simple example, the size of the delivery subset may depend on the minimum acoustic power needed to open the blood-brain barrier. This minimum acoustic power may be known a priori through experimentation or other means. Another relevant factor that may influence the size of the subset is the effects of beam propagation. Each transducer element has an angular directivity which may be dictated by a number of factors such as its size and frequency of operation. Thus, elements that are very angular relative to the target region may not be chosen for inclusion in the delivery subset.

An example of software steps that may be implemented by module 510A to determine the treatment subset in step 330 of method 300 are described herein. First, the software may request that the human operator provide a set of goals and relevant factors, such as delivering energy to a region of the brain with a certain amount of acoustic power. These goals and factors may be presented in the form of a drop down menu, checkboxes, or radio buttons to allow the operator to choose from one or more options. The software may then generate a model of the patient's head using the pre-op images and head model generation module 510H. Given the head model, and the prescribed goals, the location and orientation of ultrasound transducer elements that may be used to deliver ultrasound energy to the target region is calculated. This step may involve a process of optimization where the one or more goals and factors are parameterized, and the optimization process involves selecting a configuration yielding the highest "score". The parameterization process may optionally and beneficially take into account user assigned weights. The final selection of the delivery subset may be made manually be the human operator or automatically by the software.

In ultrasound system 210 (see FIG. 4), following the selection of the delivery subset, a subset of elements in ultrasound transducer assembly 220 may be selected to operate in treatment mode. This may involve providing instructions to all elements within subset 425A, for example, to begin transmitting ultrasound at a given transmit delay and frequency. In the configuration shown in FIG. 7A, control signals may arise from peripheral controls and I/O module 510G to inform the angle that each joint of an arm 715 should be positioned. The final result should result in arm 100's end effector (i.e. where the transducer is located) to be at the calculated position.

In the configuration shown in FIG. 7B, a human operator may manually position transducer 760B such that it is placed at the desired location with guidance from software in ultrasound system 750. Sensors on transducer 760B may detect whether the desired location has been reached and may give feedback to the operator if adjustments are required.

Where the calculations and selection are performed automatically, in addition to all of the factors discussed above, control and computation block 510 may be guided by goals such as, but not limited to, selecting a subset or a transducer that can open the blood-brain barrier to allow drugs to be delivered with the least amount of acoustic power, or in the shortest amount of time given a specific acoustic power setting.

Multiple Subsets

In some embodiments two or more subsets are generated. Each subset comprises one or more transducer elements that may be excited in a coordinated manner so that the ultimate effect is to open the blood-brain barrier at region(s) where their beam patterns intersect. Further, the subsets need not be contiguous. One advantage of multiple non-contiguous subsets is that power delivered to the intervening tissue can be minimized, while delivering the required power at one or more target region(s).

The calculation of which subsets are to be chosen to deliver ultrasound energy to a target region may depend on a number of factors such as, but not limited to, the number of target regions and the size of each region. If the target region is small, it is possible that a subset with contiguous elements may be selected. On the other hand, even for a small region, if it is determined that the intervening tissue may be at potential risk (perhaps due to high acoustic power being needed for a target region located far from the transducer elements), then non-contiguous subsets may be more appropriate. Where there are multiple target regions, or target regions that are large (that can subsequently broken up into multiple smaller regions), each region may be associated with its own calculations and its own delivery subset(s).

In the configurations illustrated in FIGS. 7A and 7B, it is noted that it is possible that a subset of elements that is fewer than the total elements present in a treatment transducer may be chosen. The size of this smaller subset may be chosen in a manner similar to the methods described for ultrasound transducer assembly 220 in FIG. 4.

Alternative Determinations of Delivery Subset

In some embodiments, the delivery subset may be pre-determined, or it can be found via reference to a look up table (LUT). As an example, gliomas are a common type of brain tumor that often develops in the brainstem. Therefore, it may be advantageous to construct ultrasound transducer assemblies (such as one shown in FIG. 4) where treatment transducer elements are localized around the back of the head to deliver ultrasound to the region of the blood-brain barrier that is closest to the brainstem. No calculations would have to be performed in this scenario to determine the subset of treatment elements to be used. This may reduce the cost of construction and maintenance of the device, as well as reduce the computational complexity of the systems used during treatment.

In other embodiments, an ultrasound transducer assembly may include several elements and a determination of the subset of elements to be used may be established through reference to a LUT. For example, based on empirical analysis from a priori experimentation and analysis on a patient's pre-op image, a LUT can provide data indicating where on a patient's head is ultrasound energy most likely to be able to reach a target region. A subset/subsets may then be chosen based on this result to deliver the treatment. In configurations where a transducer is being used (i.e. FIGS. 7A and 7B), reference to a LUT may be used to obtain the desired positions and orientations based on relevant factors such as the ones above.

In other embodiments, all available transducer elements may be configured to deliver ultrasound energy for treatment. Amplitude or other transmit parameters may be determined for each treatment based on a number of factors. These factors may include, but are not limited to, the distance from an element to the target region, the angle between the produced ultrasound beam and the target region, and the properties of intervening tissue. Where it is undesirable to insonate the target region using a certain elements, such elements may be set to transmit at an amplitude of near 0 dB.

Transmit Modes

Figure 14A:
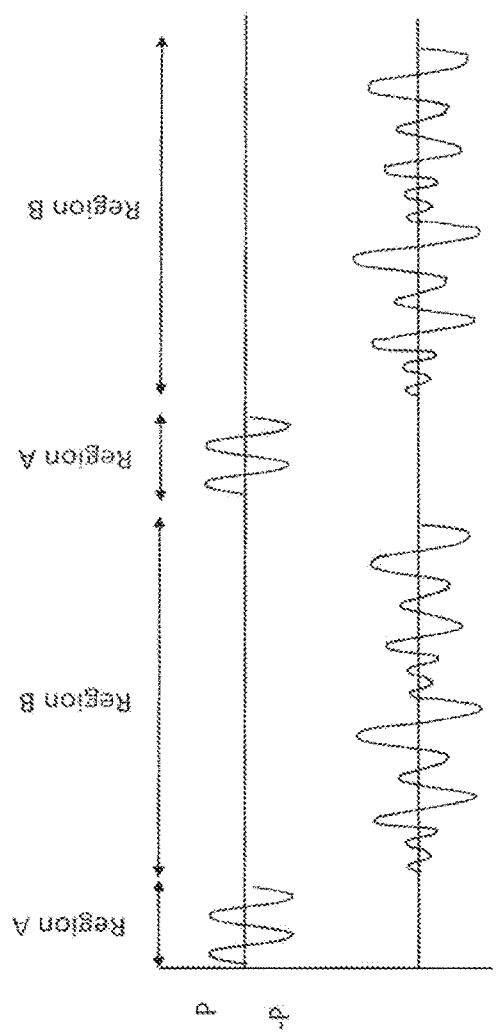
FIG. 14A is a graph illustrating example waveforms of ultrasonic energy that may be transmitted and received from an element that operating in an imaging mode.

In the various configurations of the systems described above, and in equivalent configurations, some transducer elements may be operable to transmit and receive whereas some other transducer elements may only have the ability to transmit. FIG. 14A illustrates an example waveform produced and received at a transducer element that is capable of operating in an imaging mode. In this mode, the element can both transmit and receive ultrasonic energy. Two graphs are illustrated in this figure—one for transmit operations and another for receive operations. In region A, the element is excited by a two-cycle pulse at a frequency of 2 MHz at amplitude P. This is followed by region B, where the element receives echo data from the skull as a result of the transmission. After a period of time, the element is excited again. This cycle is repeated as necessary to form images.

Figure 14B:
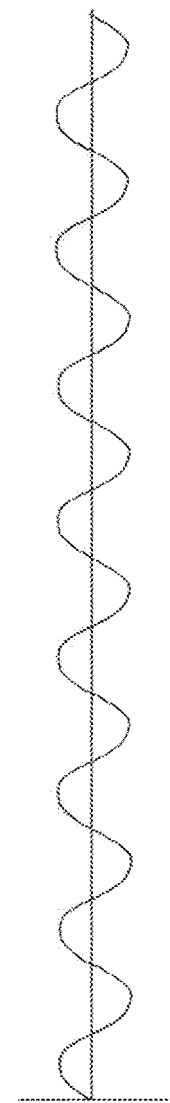
FIG. 14B is a graph illustrating example waveforms of ultrasonic energy that may be transmitted by an element operating in a treatment mode.

FIG. 14B illustrates an example waveform produced by an element that is capable of operating in a treatment mode. This element is shown to be excited by a much lower frequency, such as 0.5 MHz, and is also excited for a much longer time (8 cycles as shown in the figure). In this mode, the element does not need to receive any data and therefore does not form any images. Elements that are only capable of transmitting may be operated only in a treatment mode, while an element that is capable of both transmitting and receiving may be operated in both imaging and treatment modes.

There are several advantages to configuring transducer elements such that some are capable of transmitting and receiving, while others may only transmit. One advantage is the cost for implementing systems described herein may be reduced by making some elements capable of only transmitting. Here, the electronics and the processing needed for receiving and processing ultrasound echo data need not be included for these elements. It may be advantageous to place elements that that operate only in treatment mode (i.e. transmitting only) adjacent to areas where the attenuation of the skull is high and where imaging will typically not be performed.

On the other hand, it may be advantageous to have elements that operate only in imaging mode (i.e. transmitting and receiving) in some situations. As will be explained elsewhere herein, these elements may be used to monitor the delivery of drug. Further, having elements that can both operate in imaging mode and treatment mode can also be advantageous in some situations. It has been stated that most humans have low acoustic attenuation acoustic windows adjacent to the temples. If the target regions were in the vicinity of these areas, the same elements that form images may also be best suited to insonate the target regions.

Contrast Agent Imaging

Contrast imaging is a technique used in ultrasound imaging to enhance signal from the tissue. In contrast imaging, micro-bubbles are injected into the circulatory system. When insonated by ultrasound energy, provided that the bubbles do not break, the bubbles vibrate and reflect back energy at harmonic frequencies. Thus in a typical case, if the energy of transmission is at a frequency of f0, the bubbles reflect back energy at f0, and at other frequencies such as 2f0. The reflections from the bubbles are quite strong compared to typical reflection from tissue interfaces. Images can thus be formed of the areas where the tissue is vascularized. For the purposes of imaging the brain and providing treatment, microbubble techniques may be modified and adapted as described below.

In some embodiments, different types of microbubbles are used. In a non-limiting example where two types of microbubbles are used, one type of microbubble may be referred to as "imaging microbubbles" and the other may be referred to as "treatment microbubbles". For greater clarity, the microbubbles used in connection with opening the blood-brain barrier are referred to as treatment microbubbles. In some embodiments, these microbubbles may be supplied to the patient through IV system 230 pictured in the ultrasound systems depicted in FIGS. 2, 7A and 7B.

Figures 15A, 15B:
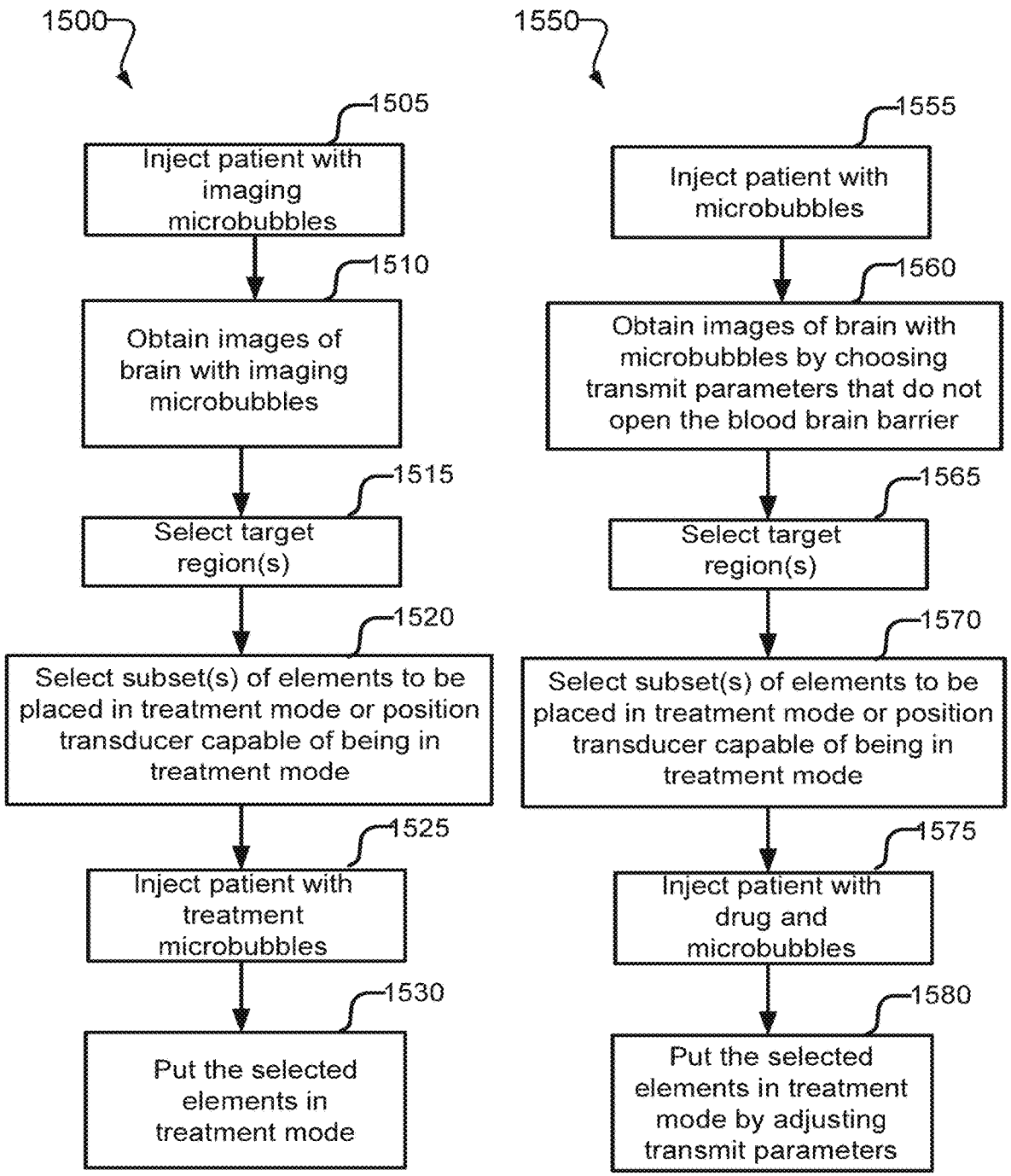
FIGS. 15A-15B are flow charts for example methods that employ the use of different types of microbubbles for imaging and for facilitating treatment.

FIG. 15A shows an example method 1500 illustrating the use of imaging microbubbles. Initially, in step 1505, the patient is injected with imaging microbubbles. The microbubbbles travel to the brain where they can be used to facilitate imaging the brain. For the sake of simplicity, it is assumed that all transducers/transducer elements in this example are capable of operating in both imaging and treatment modes. In step 1510, images of the brain are obtained using ultrasound transducers with the aid of the imaging microbubbles. In this example, the transmit parameters may be chosen such that the imaging microbubbles are caused to vibrate non-linearly. As the signals from the microbubbles are typically strong, it may be possible to use higher receive frequencies than is typically used for imaging the brain. In a non-limiting example, the imaging transducer may operate at frequencies of 2 MHz transmit and 4 MHz receive. Other combinations are also possible.

When performing imaging with the imaging microbubbles, other transmit and receive parameters such as, but not limited to, transmit power, transmit and receive apodization, receiver gain and receiver filter, may also be adjusted accordingly. These parameters, in particular the transmit parameters, may be chosen such that the imaging bubbles are stable and do not break for a sufficient period of time before imaging can be performed. Some parameters that are known to have an effect on microbubble stability are transmit power and transmit frequency. Thus for imaging the brain, a low power transmission may be used that is delivers sufficient energy to the targeted regions but not high enough to break the microbubbles during the imaging period. Once images of the brain are obtained in this manner, in step 1515, the target region or regions may be selected (using the methods described for step 325 of method 300, for example). Prior to this, however, the images obtained using the imaging microbubbles may be used in registering the pre-op image(s) to the ultrasound image (i.e. step 320 of method 300).

The use of microbubbles in ultrasound imaging compensate for the attenuation of the skull, increasing resolution and penetration depth. Therefore in some embodiments, imaging subsets or transducers are not required to be placed adjacent to low attenuation acoustic windows to form images of the brain when appropriate microbubbles are used. In some cases signals from the imaging microbubbles are strong enough that, target regions may be selected based entirely on the ultrasound image. For example, it may be possible that a target region or tumor in the brain is highly vascularized. In these scenarios, it may be possible to discern these areas in the ultrasound image when imaging microbubbles are used.

Treatment Microbubbles

After the target regions are selected in step 1515, method 1500 continues to step 1520 where one or more transducers, or subsets of transducer elements are selected and/or positioned for delivering ultrasound energy to a target region. The methods for accomplishing this may be substantially similar to the ones described above for step 330 of method 300 for the different ultrasound system configurations. Once the subset(s) of elements are selected, or treatment transducer(s) are appropriately positioned, in step 1525, the patient is injected with treatment microbubbles.

In some embodiments, the treatment microbubbles may contain the drug. In other embodiments, the drug may be injected independent of the treatment microbubbles, where the microbubbles serve to assist in the opening of the blood-brain barrier, but not to deliver drugs themselves. Now in box 1530, the subset or subsets of elements that were chosen to be in the treatment mode, are activated and the treatment microbubbles are caused to vibrate violently and or break, causing the blood-brain barrier to open up to allow the passage of drugs.

The treatment microbubbles and the imaging microbubbles may be different in a number of ways, and a partial list of these differences is now provided. Microbubbles can be manufactured so that they respond to different frequencies. For example, microbubbles that break at lower frequencies may be used in conjunction with treatment transducers. Certain microbubble characteristics such as, but not limited to, its size and content may impact its response. In some embodiments, imaging microbubbles may be air or liquid filled whereas treatment microbubbles may be filled with a drug. Other differences may exist and these differences may be exploited to allow for the selection of ultrasound system parameters such that the microbubbles facilitate imaging or treatment delivery operations.

Method 1550 in FIG. 15B illustrates another variation of the concept described above where the imaging and treatment microbubbles are the same. At step 1555, the patient is also injected with microbubbles. Method 1550 continues to step 1560 where images of the brain are obtained by choosing the ultrasound transducer transmit parameters such that the microbubbles facilitate imaging and do not to disrupt the blood brain barrier. These transmit parameters may include, but are not limited to, a transmit power at or below a certain threshold, transmit frequency, burst length, and pulse repetition frequency. The target regions are selected in step 1565 followed by the selection of subset or subsets of elements that are to be paced in treatment mode in step 1570. Now in step 1575, the drug, and optionally, more microbubbles, is injected into the circulatory system. In step 1580, transmit parameters of the delivery subset are adjusted so that the microbubbles vibrate more violently and the blood-brain barrier is opened so that the drug may be delivered.

Associate Drugs to a Transmit Sequence

In some embodiments, while a delivery subset is operating in treatment mode, the transmit parameters may specifically be selected based on the drug being delivered. As an example, through prior knowledge and/or experimentation, it may be known that drug A is delivered optimally with a 10 cycle pulse at 0.5 MHz with a pulse repetition frequency of 1 KHz for a period of 10 minutes, while drug B is delivered optimally with a 15 cycle pulse at 0.25 MHz with a pulse repetition frequency of 1.2 KHz for a period of 15 minutes. These optimal values may depend on a number of factors such as, but not limited to, results obtained in animal trials, results obtained in human trials, knowledge of drug composition, knowledge of microbubble composition, and body habitus of the patient.

In a non-limiting implementation of this concept, an imaging and treatment system may include a bar code reader, a scanner, or another type of input device that reads information from a label on the container of a drug. Once the system reads this information, the system can access memory storage such as a LUT where an optimal set of transmit parameters are stored for one or more drugs. This set of parameters may include one or more parameters such as, but not limited to, frequency, transmit voltage, pulse length and pulse repetition frequency. When instructed to do so, the imaging and treatment system may access this stored information and operate ultrasound transducers in accordance with these parameters. In other embodiments, an authorized medical personnel may manually enter relevant information such as, but not limited to, information about the drug and body habitus.

In some embodiments, the system can be programmed such that if drug information is not entered by one of the methods described above or by any other method, then ultrasound transducers are prevented from operating in treatment mode. According to a more specific embodiment, requiring information about the drug also allows the use of this action to enable a billing function. The system may send a report or send an email about how the responsibility for reimbursement for the drug and/or treatment is to be shared amongst various parties.

Reducing or Eliminating Standing Waves

Standing waves within the cranial cavity can present a significant risk to patients. Standing waves may be created during both imaging and treatment modes. Using non-uniform pulse repetition intervals may reduce or eliminate the possibility of creation of standing waves. While this method may be advantageous for imaging operations, it may not be ideal for the treatment mode. As explained above, drugs may be most effectively delivered with a certain set of transmit parameters. This may involve exposing the target region to ultrasound for a certain amount of time. In some embodiments, to provide the necessary exposure time and to reduce or eliminate the possibility of generation of standing waves, different subsets (such as subset 425A in FIG. 4) of elements may be used to deliver energy.

Figure 16:
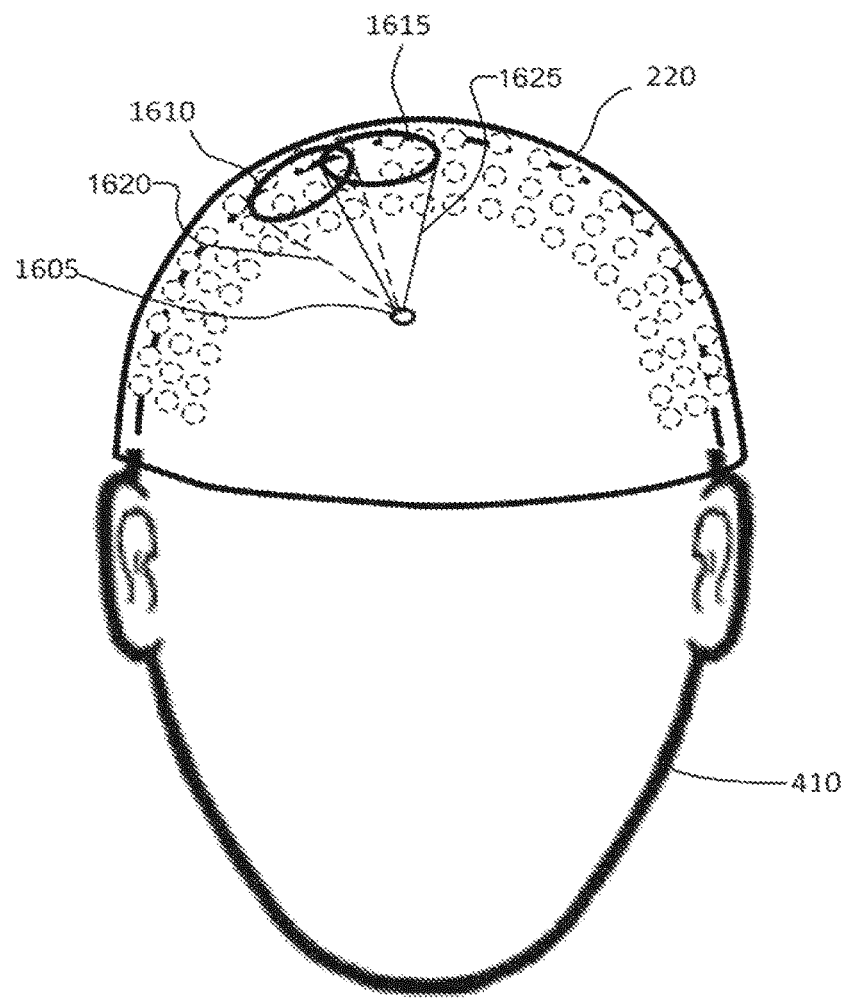
FIG. 16 is a schematic illustration showing how standing waves may be reduced or eliminated.

FIG. 16 illustrates an example embodiment of how different subsets may be chosen to insonate the same target region. This method may facilitate educing or eliminating standing waves while delivering the required dosage of ultrasound to the target region. Target region 1605 is initially insonated with transmit treatment pulses by subset 1610 for a period of time. The transmit delays of the elements of this subset are chosen such that region 1605 is insonated with subset 1610. The focusing of the ultrasound energy emitted by the elements in subset 1610 is depicted by dashed lines 1620 that extend from subset 1610 to target region 1605. At a subsequent but successive time, subset 1615 may be used to transmit treatment pulses for another period of time. The focusing of the ultrasound energy emitted by the elements in this subset is depicted by the solid lines 1625. Although FIG. 16 shows a region of overlap between subsets 1610 and 1615, configurations where there is no overlap may also be utilized. Although only two subsets are illustrated in the figure, more than two subsets may be utilized in the performance of this technique.

In some embodiments, software that implements the above method may request the user to input the number of treatment subsets to be used. Goals for each subset may be further specified. Factors that may be programmed include, but are not limited to, maximum allowable off-axis angle, maximum time each subset may be active, and maximum amount of subset overlap. For example, an entered set of goals may be to find subsets that are within 3° of the shortest distance to the target region (which may be specified as 0°) and with the least amount of overlap. Given these example instructions, the software may find subsets whose centers are 3° or less from the shortest distance and then determine the appropriate size of these subsets, the order in which they are active, and the transmit parameters for each subset.

In some embodiments, such instructions may be entered as part of the software programming process for an ultrasound system. In other embodiments, a user may provide instructions for an ultrasound system through a user interface. Once the instructions have been provided to the ultrasound system, systems control module 510F may generate and provide control signals to the selected subsets to transmit ultrasound energy to the patient.

Although illustrations of this method refer to subsets of transducer elements, the same concepts may be applied to configurations utilizing transducers, such as those shown in FIGS. 7A and 7B. In these cases, multiple individual transducer elements capable of operating in treatment mode may be grouped together to accomplish these methods. In other embodiments, the groups of treatment elements may be located in different transducers.

Building a Volumetric Image

In conventional ultrasound imaging systems, 3D or 4D images are typically created by a 2D transducer with the elements being in the same plane, a 1D array being "wobbled" in an elevation dimension, or a 1D rotating transducer such as those used in transesophageal imaging. Building a volumetric image may be desirable in the ultrasound systems described herein because a more representative model of the brain's structures allow for higher accuracy in performing comparisons with pre-op images during the registration process. In another example, where the resolution of structures obtained by ultrasound imaging is high enough (e.g. through the use of microbubbles), a volumetric ultrasound image may allow for a target region to be selected. However, in the configuration shown in FIG. 4 for example, the elements within ultrasound transducer assembly 220 are arranged differently compared to typical transducer arrangements. Therefore, different scanning techniques may be required to form 3D or 4D images with the systems described herein.

Figure 17:
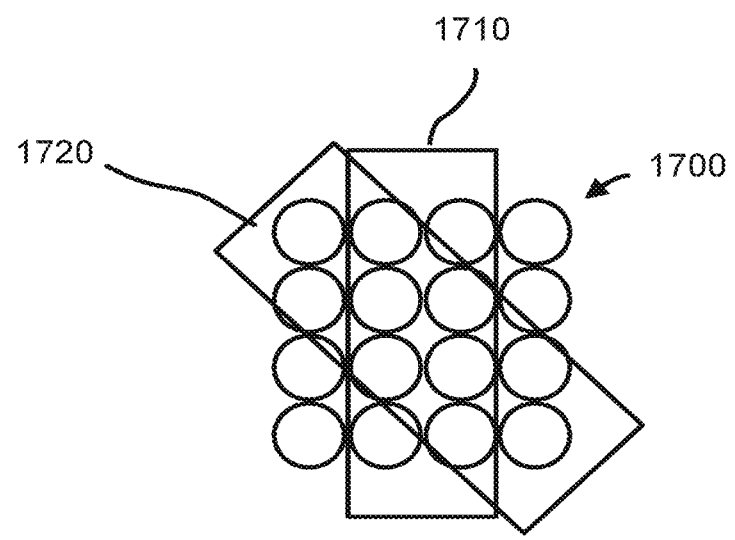
FIG. 17 is a schematic illustration showing how the same subset of elements may be used for different scanning planes.

In some embodiments, different imaging planes may be used with the same subset of elements. In any subset of elements containing multiple elements, the elements can be arranged electronically in various ways such as, but not limited to, in an array configuration or in a concave curvilinear configuration. The orientation of the curvilinear configuration may also be chosen as desired. An example non-limiting embodiment of this concept is shown in FIG. 17. Here an array of elements 1700 is illustrated. This array of elements may be part of the subset 420A of ultrasound transducer assembly 220 in FIG. 4, for example. As each of the elements within this array may be independently cabled and therefore controllable via an ultrasound system, various scanning planes may be achieved electronically. Two such example groups are illustrated by 1710 and 1720. Any element that does not lie completely within the dashed lines may be excluded from the group. The electronic delays calculated by the modules 510A and 510B may be such that the scanning planes of each of groups 1710 and 1720 are perpendicular to the plane of FIG. 17 (into the page), but parallel to the long side of the boundaries of these groups.

Through these methods, multiple scanning planes may be generated. The images obtained from these scanning planes would interrogate different anatomical planes. Thus by generating multiple planes along different scanning planes, a volume may be scanned and a volumetric image be generated.

In other embodiments, different imaging planes may be used to fill in missing volumetric information. These different imaging planes need not have the same orientation or angle or location with respect to each other. However, because an image plane's 6DOF position is known in a common reference frame, it can be placed alongside other images in the same coordinate system such that a volumetric image can be constructed. This method to construct a volume may be advantageous because data about the entire volume of the brain is often incomplete. Partial volume reconstruction as described allows for the available image data to be put towards meaningful uses. In a more specific embodiment, interpolation of RF echo data can be used in a volume construction data set to fill-in missing data elements.

Synthetic Aperture Imaging

Any suitable ultrasound imaging technology may be applied. Example, ultrasound imaging technologies include beamforming technologies and synthetic aperture imaging technologies Synthetic aperture imaging allows for the formation of an image with fewer transducer elements compared to what is needed in a fully populated aperture. The concepts of synthetic aperture imaging may be modified for the purposes of producing ultrasound images of the brain. In some embodiments, different transducer elements may be used for each transmit operation. After each transmission, the echo may be received at multiple elements, and the echo data may be digitized and stored. An ultrasound system may then process the various pulse-echo response pairs to synthesize and construct a higher resolution image than would normally be possible with the number of elements involved.

Another advantage that can be gained by using synthetic aperture imaging is that as different elements are being used for transmission, the possibility of generating standing waves is reduced or eliminated. Methods of synthetic aperture imaging described herein may be applied to all of the various ultrasound system configurations discussed.

Insonating Regions Close to the Surface of the Skull

Additional challenges are encountered when attempting to insonate target regions close to the surface of the skull. For example it is difficult to position elements such that they are parallel to the surface of the skull at the point of contact and still direct energy to the target region. Focusing the ultrasonic energy may also be challenging due to the low frequency and short distance between the target region and the elements. In some embodiments, subsets of elements that are relatively distant from the target region are be chosen such that these subsets are parallel or nearly parallel to the skull at the point of contact. In a non-limiting example, a target region on the left side of the head near the ears may be insonated by a subset of elements from the right side of the head. Using appropriate transmit parameters, the blood-brain barrier on the left side can be made to open up to allow drugs to pass. In addition to location, transmit parameters such, as but not limited to, frequency and power may be adjusted to insonate such target regions from a distance.

In another embodiment, transducers (such as those shown in FIGS. 7A and 7B) may be positioned at a distance away from the skull. A stand-off material may be placed between said transducers and the skull such that the two components may remain coupled. Stand-off materials are typically soft and gelatinous. The stand-off material may be selected such that essentially no attenuation of ultrasound occurs through the material. In a non-limiting example, the speed of sound through this material may be 1540 m/s. Additionally, the thickness of the material may be anywhere between 1 cm to 5 cm. Through this technique, the transducers can be placed in a parallel or nearly parallel manner to the skull. As the distance between the target region and the elements is larger, issues of focusing at short distances are minimized or removed. It should be noted that these methods of operating transducer elements close to a target region are equally applicable to transducers or subsets operating in imaging mode.

Stand-off materials may also be used optionally and beneficially in configurations where there are one or more transducer elements dispersed over an assembly (such as that shown in FIG. 4). In some embodiments, a layer of stand-off material may be placed around and in contact with a patient's head. Ultrasound transducer assembly 220, for example, may be placed over the material, with transducer elements 415 in contact with it. The properties and thicknesses of the stand-off material may be selected such that it is able to be in contact with elements 415 and does not exert a reaction force high enough that the ability to control the orientation of elements 415 is inhibited. This allows for standard sized ultrasound transducer assemblies to be used across a range of patient head sizes.

Subset Specific System Parameters

In some embodiments, each subset or transducer may be operated with its own set of parameters such as, but not limited to, transmit parameters, receive parameters, number of elements, element configuration, aperture dimensions. In a non-limiting example, a subset operating in treatment mode in the vicinity of the temporal bone may operate at a higher frequency, for example 2 MHz, compared to a subset near the top of the head that may operate at 0.5 MHz. Similarly, the active aperture near the temporal bone may include elements that are generally within a circle of radius 20 mm whereas the aperture near the top of the head may generally be rectangular in shape with dimensions of 70 mm by 10 mm.

Subset or transducer parameters may be calculated automatically or manually. In some embodiments, automatic calculations may be carried out by control and computation block 510. These calculations may include information about the location of the subset/transducer on the skull and may calculate parameters based on this information. Thus, parameters may be optimized for each subset or transducer depending on location and what imaging or treatment goals have been defined. Regardless of whether the subset or transducer parameters are calculated manually or automatically, transmit and receive parameter computation modules 510A and 510B may ensure that no safety limits such as acoustic or thermal limits are violated. Application of these concepts may allow for the accommodation of the local conditions of the skull, the tissue in the vicinity of the elements, and the tissue that is insonated.

Fiducials

Some patients may have objects in their head, such as screws or dental implants, that may be observable in ultrasound, MRI, and CT scans. In some embodiments, such objects may be used as fiducial markers to improve the accuracy of registration. In a non-limiting example, a dental implant may be imaged by one or more transducer elements. If the location of the transducer element(s) were known, an ultrasound transducer assembly (see ultrasound transducer assembly 220 in FIG. 4) or transducer can be placed in relation to the dental implant. If the location of the same implant is known in a pre-op image, then registration of an ultrasound image to the pre-op image may be performed against the dental implant. This method offers an alternative to registering pre-op and ultrasound images that does not require transducer elements to be located specifically at low acoustic attenuation windows.

Confirmation of Dose Delivery

Contrast agents such as microbubbles may be used to facilitate the delivery of drugs and to obtain confirmation that a drug has been delivered. In some embodiments, ultrasound transducers or subsets may be interspersed with elements that are specially tuned to receive energy released from microbubbles as the blood-brain barrier opens up. This energy may be in the sub-harmonic range or the harmonic range. In a more specific embodiment, one or more receive only elements are tuned to detect these specific frequencies to confirm the delivery of an ultrasound dose and/or drug.

Display and User Interface

Figure 18:
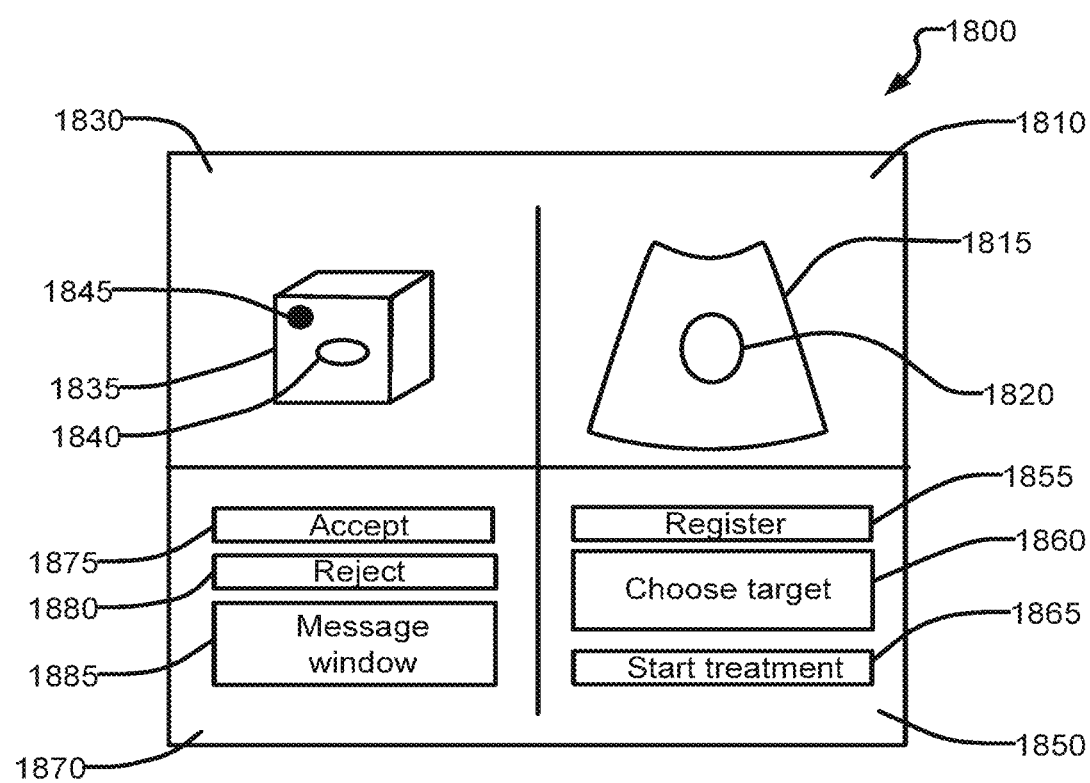
FIG. 18 illustrates one configuration of a user interface that a user may use to interact with an ultrasound system.

FIG. 18 illustrates a non-limiting example of a display and user interface 1800 that may be provided to an authorized person such as a doctor to interact with an example ultrasound system described above. In this configuration, the display may contain four windows, 1810, 1830, 1850 and 1870. In window 1810, the ultrasound image from a low attenuation acoustic window may be displayed. Image 1815 is obtained from a low attenuation low attenuation acoustic window with circle of Willis 1820 pictured inside it. In window 1830, pre-op image 1835 may be simultaneously displayed. Pre-op image 1835 may be a 3D rendering of images obtained from MRI scans, for example. The circle of Willis labelled in the pre-op image as 1840, but physically it is the same structure as 1820 in ultrasound image 1815.

As initial steps not shown in this illustration of a user interface 1800, the user may be requested by the ultrasound system to import pre-op images of the patient's brain. The user may then be instructed to place imaging transducers at low attenuation acoustic windows to allow the ultrasound system to collect images. These steps relate to steps 305 and 310 of method 300 respectively. In other embodiments of a user interface, instruction and confirmation messages may be provided by the ultrasound system.

A suitable user interface may be provided to allow the user to register the two images. FIG. 18 illustrates workflow window 1850 with a number of user selectable boxes 1855, 1860, and 1865. The user may select box 1855 to begin the process of registration of an ultrasound image with the pre-op image(s). After this selection, user interface 1800 may ask the user to select an ultrasound image that may be used for registration. If live imaging through a low attenuation acoustic window is being performed, the system may halt live imaging and provide the user the option of scrolling through images in window 1810 that have been just recently acquired and stored, and choosing an image from this set of images. In a conventional ultrasound imaging system, the storing function is called the "cine" function. Once an appropriate image is selected, the user may be asked to outline a structure within the image (such as circle of Willis 1820 in this example). This process is called segmentation.

Segmentation may be carried out automatically, manually, or in a combination of the two. In the present example, a doctor may provide an initial outline of the circle of Willis 1820. Ultrasound systems described herein may optionally and beneficially provide a color Doppler imaging mode to aid the segmentation process. Operating in this mode allows for blood flow in the circle of Willis to be detected and displayed, making the boundaries of the vessels that form the circle of Willis easily distinguishable. The user can therefore easily draw an outline of the Circle of Willis using the colored vessels against the black and white image of the rest of the brain tissue. The ultrasound system may proceed with the next step, or alternatively use the manually drawn boundaries as a basis for segmentation algorithms programmed internally to generate a more accurate segmentation. This selection process relates to step 310 of method 300.

Once segmentation is complete, user interface 1800 may request for the selection of a plane that most closely matches the segmented image. Again, this may be carried out manually, automatically or in a combination of the two. In an automatic process, the ultrasound system may look within pre-op image 1835 to try and find an image plane that most closely matches the segmented ultrasound image. In a combined operation, user interface 1800 may display a fused ultrasound and MRI image in window 1830, after automatically determining a plane within the MR image, and ask the user to make a determination on if that match was acceptable.

Window 1870 may be used to display messages and accept inputs from the user. Selectable boxes such as accept box 1875 and reject box 1880 may be displayed to accept inputs from the user. The user may therefore indicate acceptance of the match between the ultrasound and pre-op image, or may direct the ultrasound system to continue to find a better match. Other user interface elements may also be provided to the user to guide the matching process. The selection of a desirable plane in the pre-op image may be used as the starting point in the registration process (this may reflect step 320C2 in method 320C, for example). As the ultrasound system performs the process of registration, it may display a status indicator in message window 1885. Message window may notify the user when registration is completed and/or provide further instructions.

Subsequently in window 1850, user interface 1800 may ask the user to select a target region in box 1860, corresponding to step 315 in method 300. As described previously, the target region may be chosen in the MR image. In this illustration, the user may point to a region such as region 1845 and select it as the target region. It should be noted that this step may be performed at any point after a pre-op image has been obtained. Its inclusion in these steps only serves to illustrate how it may be performed alongside other steps in a common user interface.

The ultrasound system may automatically select a region around the area selected by the user. This region selection may be guided by preprogrammed data entered into the ultrasound system a priori. Alternatively, user interface 1800 may allow the user to modify the boundary of the automatically selected target region, or to select it entirely manually. After the user indicates they are satisfied with the size and shape of the target region (through the use of message box 1885 and boxes 1875 and 1880 in window 1870), user interface 1800 may then ask the user to begin the treatment. This process reflects an example embodiment of step 325 of method 300 and may provide the coordinates of the target regions as output. Start treatment button 1865, which may have previous been greyed out, may become selectable, and when selected may trigger a number of actions.

After starting treatment, the ultrasound system may calculate the delivery subset as explained above in step 330 of method 300. Following this, the ultrasound system may move a treatment transducer to the appropriate location on the head in the configuration shown in FIG. 7A, or select the treatment subset(s) in the configuration shown in FIG. 4. Where a treatment transducer is controlled manually, such as in the configuration shown in FIG. 7B, the current treatment transducer coordinates may be displayed in the message window 1885 along with the desired calculated coordinates. When the user has correctly placed the transducer at the desired coordinates, message window 1885 may display a message indicating this. Other methods of guiding the user to the desired location are possible.

Once the treatment elements are selected or the treatment transducer is in the appropriate location, the ultrasound system may send signals to the IV pump and treatment transducer elements to coordinate the timing of the delivery of ultrasound with the operation of the IV pump. Depending on signals obtained from the transducer and/or other sensors, user interface 1800 may display when the blood-brain barrier has opened up, or other relevant status updates. This information may be calculated in real-time or may be based on empirical analysis from a priori experimentation. A message may be displayed in message window 1885 once a drug has been delivered indicating that treatment is completed or that the user should proceed to treat another region.

Interpretation of Terms

Unless the context clearly requires otherwise, throughout the description and the

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Implementations of the invention may comprise any of specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a system as described herein or for an ultrasound machine as described herein or for a module as described herein may implement methods as described herein by executing software instructions in a program memory accessible to the processors and/or by processing data according to logic configured in a logic circuit or configurable device such as an FPGA and/or by processing data in an ASIC or other logic circuit configured to perform the method steps described herein.

A group of modules as described herein may be implemented using separate hardware (e.g. separate processors and/or configurable logic circuits and/or hard-wired logic circuits) but two or modules may also share some or all of a hardware platform. For example two or more modules may be implemented by common data processor(s) and/or configurable logic circuits and/or hard-wired logic circuits configured by software instructions or otherwise to perform the functions of each of the two or more modules.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Some aspects of the invention may be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some implementations, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary implementations of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described implementations that would be apparent to the skilled addressee, including variations obtained by: replacing features, elements and/or acts with equivalent features, elements and/or acts; mixing and matching of features, elements and/or acts from different implementations; combining features, elements and/or acts from implementations as described herein with features, elements and/or acts of other technology; and/or omitting combining features, elements and/or acts from described implementations.

It is therefore intended that claims hereafter introduced are interpreted to include all such modifications, permutations, additions, omissions, and sub-combinations as may reasonably be inferred. The scope of the claims should not be limited by the preferred implementations set forth in the examples, but should be given the broadest interpretation consistent with the description as a whole.

What is claimed is:

1. An ultrasound treatment system operable to deliver ultrasound energy to a patient's brain, the ultrasound treatment system comprising:
    a treatment ultrasound transducer comprising a plurality of treatment elements, the treatment ultrasound transducer locatable to deliver ultrasound into the head of the patient;
    a data store;
    a plurality of position sensors configured to detect relative movement between the head of the patient and the treatment ultrasound transducer, wherein at least a first of the plurality of position sensors is coupled to the treatment ultrasound transducer and a second of the plurality of position sensors is placed on the head of the patient; and
    a data processor configured to:
        determine a registration transformation which transforms coordinates of at least one target region identified in a previously obtained image in the data store to coordinates of the ultrasound treatment system;
        determine an initial treatment ultrasound transducer location from which to deliver ultrasound treatment energy from the treatment ultrasound transducer to the at least one target region based at least in part on the registration transformation; and
        monitor outputs from the plurality of position sensors to determine the detected relative movement between the head of the patient and the treatment ultrasound transducer;
        determine an updated treatment ultrasound transducer location from which to deliver ultrasound treatment energy from the updated treatment ultrasound transducer to the at least one target region based at least in part on the detected relative movement; and
        control the treatment ultrasound transducer to deliver treatment ultrasound energy from the updated treatment ultrasound transducer location to the at least one target region with an energy sufficient to open the blood brain barrier of the patient at the at least one target region.

2. The system of claim 1 wherein the data processor is configured to position the treatment ultrasound transducer to the updated treatment ultrasound transducer location, wherein a biological effect of delivering the treatment ultrasound energy and opening the blood brain barrier at the least one target region is not imaged during the treatment.

3. The system of claim 1 wherein the treatment ultrasound transducer comprises a plurality of elements and the data processor is configured to determine a subset of the plurality of elements to deliver the treatment ultrasound energy based at least in part on the updated treatment ultrasound transducer location, wherein the system is not forming ultrasound images of the at least one target region during the delivery of the treatment ultrasound energy.

4. The system of claim 1 wherein the data processor is configured to monitor output from the plurality of position sensors and determine the updated treatment ultrasound transducer location after commencing delivery of the treatment ultrasound energy, wherein the previously obtained image is obtained from a source other than the treatment ultrasound transducer and the previously obtained image is not used to detect the relative movement between the head of the patient and the treatment ultrasound transducer, and wherein the control of the treatment ultrasound transducer to deliver the treatment ultrasound energy includes at least one of:
  controlling a robotic manipulator to position the treatment ultrasound transducer at a target location to deliver the treatment ultrasound energy from the updated treatment ultrasound transducer location to the at least one target region; or
  selecting a subset of the plurality of treatment elements to deliver the treatment ultrasound energy from the updated treatment ultrasound transducer location to the at least one target region.

5. The system of claim 4 wherein the data processor is configured to cause the robotic manipulator to move and to position the treatment ultrasound transducer at the target location for delivering the treatment ultrasound energy to the updated treatment ultrasound transducer location after commencing delivery of the treatment ultrasound energy.

6. The system of claim 4 wherein the treatment ultrasound transducer comprises a plurality of elements and the data processor is configured to determine the subset of the plurality of treatment elements to deliver the treatment ultrasound energy based at least in part on the updated treatment ultrasound transducer location after commencing delivery of the treatment ultrasound energy.

7. The system of claim 1 wherein the data processor is configured to monitor the outputs from the plurality of position sensors and determine the updated treatment ultrasound transducer location prior to commencing delivery of the treatment ultrasound energy and on a periodic basis during the delivery of the treatment ultrasound energy.

8. The system of claim 1 wherein the data processor is configured to monitor output from the plurality of position sensors and determine the updated treatment ultrasound transducer location before commencing delivery of the treatment ultrasound energy, wherein the plurality of position sensors are electromagnetic sensors.

9. The system of claim 8 wherein the data processor is configured to control the treatment ultrasound transducer to deliver the treatment ultrasound energy by causing a robotic manipulator to position the treatment ultrasound transducer at a target location to deliver the treatment ultrasound energy from the updated treatment ultrasound transducer location before commencing delivery of the treatment ultrasound energy.

10. The system of claim 8 wherein the data processor is configured to determine the subset of the plurality of treatment elements to deliver the treatment ultrasound energy based at least in part on the updated treatment ultrasound transducer location before commencing delivery of the treatment ultrasound energy and on a periodic basis during the delivery of the treatment ultrasound energy.

11. The system of claim 1 wherein the data processor is configured, after commencing delivery of the treatment ultrasound energy, to monitor output from the plurality of position sensors to determine whether the detected relative movement is greater than a threshold and, in response to the detected relative movement being greater than the threshold, to take corrective action related to the delivery of treatment ultrasound energy.

12. The system of claim 11 wherein the data processor is configured to take corrective action which comprises positioning the treatment ultrasound transducer to the updated treatment ultrasound transducer location.

13. The system of claim 11 wherein the treatment ultrasound transducer comprises a plurality of elements and the data processor is configured to take corrective action which comprises determining an updated subset of the plurality of elements to deliver the treatment ultrasound energy based at least in part on the updated treatment ultrasound transducer location.

14. The system of claim 11 wherein the data processor is configured to take corrective action which comprises at least one of: discontinuing delivery of the treatment ultrasound energy; and providing a warning message.

15. A method for configuring an ultrasound treatment system, the method comprising:
  providing a treatment ultrasound transducer comprising a plurality of treatment elements, the treatment ultrasound transducer locatable and selectable to deliver ultrasound into the head of the patient;
  providing a plurality of position sensors configured to detect relative movement between the head of the patient and the treatment ultrasound transducer, wherein at least a first of the plurality of position sensors is coupled to the treatment ultrasound transducer and a second of the plurality of position sensors is placed on the head of the patient;
  by a data processor:
    determining a registration transformation which transforms coordinates of at least one target region identified in a previously obtained image to coordinates of the ultrasound treatment system;
    determining at least one of an initial treatment ultrasound transducer location and a selected subset of the plurality of treatment elements from which to deliver ultrasound treatment energy from the treatment ultrasound transducer to the at least one target region based at least in part on the registration transformation;
    monitoring output from the plurality of position sensors to determine detected relative movement between the head of the patient and the treatment ultrasound transducer;
    determining at least one of an updated treatment ultrasound transducer location and an updated selected subset of the plurality of treatment elements from which to deliver ultrasound treatment energy from the treatment ultrasound transducer to the at least one target region based at least in part on the detected relative movement; and
    controlling the treatment ultrasound transducer to deliver treatment ultrasound energy from the updated treatment ultrasound transducer location to the at least one target region with an energy sufficient to open the blood brain barrier of the patient at the at least one target region.

16. The method of claim 15 comprising positioning the treatment ultrasound transducer to the updated treatment ultrasound transducer location or selecting the updated selected subset of the plurality of treatment elements, wherein the plurality of position sensors are non-imaging sensors.

17. The method of claim 15 wherein the method comprises determining the subset of the plurality of treatment elements to deliver the treatment ultrasound energy based at least in part on the updated treatment ultrasound transducer location.

18. The method of claim 15 comprising monitoring output from the plurality of position sensors and determining the updated treatment ultrasound transducer location after commencing delivery of the treatment ultrasound energy.

19. The method of claim 18 comprising positioning the treatment ultrasound transducer to the at least one of the updated treatment ultrasound transducer location and the updated selected subset of the plurality of treatment elements after commencing delivery of the treatment ultrasound energy.

20. The method of claim 18 wherein the method comprises determining subset of the plurality of treatment elements to deliver the treatment ultrasound energy based at least in part on the updated treatment ultrasound transducer location after commencing delivery of the treatment ultrasound energy.

* * * * *